(12) United States Patent
Fabian et al.

(10) Patent No.: US 8,236,058 B2
(45) Date of Patent: Aug. 7, 2012

(54) SPINE SURGERY METHOD AND IMPLANT

(76) Inventors: Henry F. Fabian, Steamboat Springs, CO (US); Larry A. Cicoretti, Poland, OH (US)

( * ) Notice: Subject to any disclaimer, the term of this patent is extended or adjusted under 35 U.S.C. 154(b) by 2020 days.

(21) Appl. No.: 11/236,068

(22) Filed: Sep. 27, 2005

(65) Prior Publication Data

US 2007/0073398 A1  Mar. 29, 2007

(51) Int. Cl.
*A61F 2/44* (2006.01)
(52) U.S. Cl. .............. 623/17.16; 623/17.11; 623/17.15
(58) Field of Classification Search .............. 623/17.11, 623/17.13, 17.15, 17.16
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,401,112 A | 8/1983 | Rezaian |
| 4,553,273 A | 11/1985 | Wu |
| 4,643,178 A | 2/1987 | Nastari et al. |
| 4,759,769 A | 7/1988 | Hedman et al. |
| 4,772,287 A | 9/1988 | Ray et al. |
| 4,820,305 A | 4/1989 | Harms et al. |
| 4,863,477 A | 9/1989 | Monson |
| 4,932,969 A | 6/1990 | Frey et al. |
| 4,932,975 A | 6/1990 | Main et al. |
| 4,946,378 A | 8/1990 | Hirayama et al. |
| 5,002,576 A | 3/1991 | Fuhrmann et al. |
| 5,071,437 A | 12/1991 | Steffee |
| 5,123,926 A | 6/1992 | Pisharodi |
| 5,156,839 A | 10/1992 | Pennell et al. |
| 5,246,458 A | 9/1993 | Graham |
| 5,314,477 A | 5/1994 | Marnay |
| 5,439,464 A | 8/1995 | Shapiro |
| 5,505,732 A | 4/1996 | Michelson |
| 5,571,192 A | 11/1996 | Schonhoffer |
| 5,772,661 A | 6/1998 | Michelson |
| 5,782,919 A | 7/1998 | Zdeblick et al. |

(Continued)

FOREIGN PATENT DOCUMENTS

EP  1506753  2/2005

(Continued)

OTHER PUBLICATIONS

Disc Orthopaedic Technologies to Introduce B-Twin Expandable Spinal Fusion System at NASS, by N.J. Monroe, dated Sep. 26 (no year given), article from PRNewswire, copyright 1996-2006 PR Newswire Association LLC, webpage (http://www.prnewswire.com/cgi-bin/stories.pl?ACCT=104&STORY=/www/story//09-26-2005/0004131865&EDATE=), USA.

(Continued)

*Primary Examiner* — Thomas C. Barrett
*Assistant Examiner* — Christine Nelson
(74) *Attorney, Agent, or Firm* — Timothy D. Bennett, Esq.; Emerson Thomson Bennett

(57) ABSTRACT

An implant has a first contact surface to contact a first vertebral body endplate and a second contact surface to contact a second vertebral body endplate adjacent the first vertebral body. The implant is deployable, when positioned within an intradiscal space between the first and second vertebral bodies, from a first non-expanded condition where the first contact surface has a first effective footprint area A1 to a second expanded condition where the first contact surface has a second effective footprint area A2. The ratio A2/A1 is at least 1.05.

10 Claims, 22 Drawing Sheets

U.S. PATENT DOCUMENTS

| | | | |
|---|---|---|---|
| 5,785,647 A | 7/1998 | Tompkins et al. |
| 5,976,187 A | 11/1999 | Richelsoph |
| 6,080,155 A | 6/2000 | Michelson |
| 6,093,205 A | 7/2000 | McLeod et al. |
| 6,193,757 B1 | 2/2001 | Foley et al. |
| 6,200,348 B1 | 3/2001 | Biedermann et al. |
| 6,206,922 B1 | 3/2001 | Zdeblick et al. |
| 6,228,022 B1 | 5/2001 | Friesem et al. |
| 6,283,966 B1 | 9/2001 | Houfburg |
| 6,395,031 B1 | 5/2002 | Foley et al. |
| 6,395,034 B1 | 5/2002 | Suddaby |
| 6,402,785 B1 | 6/2002 | Zdeblick et al. |
| 6,409,766 B1 * | 6/2002 | Brett .................. 623/17.16 |
| 6,471,724 B2 | 10/2002 | Zdeblick et al. |
| 6,488,710 B2 | 12/2002 | Besselink |
| 6,514,260 B1 | 2/2003 | Zdeblick et al. |
| 6,524,318 B1 | 2/2003 | Longhini et al. |
| 6,565,574 B2 | 5/2003 | Michelson |
| 6,575,981 B1 | 6/2003 | Boyd et al. |
| 6,599,292 B1 | 7/2003 | Ray |
| 6,626,943 B2 | 9/2003 | Eberlein et al. |
| 6,648,895 B2 | 11/2003 | Burkus et al. |
| 6,695,851 B2 | 2/2004 | Zdeblick et al. |
| 6,706,068 B2 | 3/2004 | Ferree |
| 6,709,458 B2 | 3/2004 | Michelson |
| 6,712,818 B1 | 3/2004 | Michelson |
| 6,712,819 B2 | 3/2004 | Zucherman et al. |
| 6,712,825 B2 | 3/2004 | Aebi et al. |
| 6,716,247 B2 | 4/2004 | Michelson |
| 6,719,794 B2 | 4/2004 | Gerber et al. |
| 6,723,096 B1 | 4/2004 | Dorchak et al. |
| 6,730,127 B2 | 5/2004 | Michelson |
| 6,733,535 B2 | 5/2004 | Michelson |
| 6,743,234 B2 | 6/2004 | Burkus et al. |
| 6,746,484 B1 | 6/2004 | Liu et al. |
| 6,749,636 B2 | 6/2004 | Michelson |
| 6,758,849 B1 | 7/2004 | Michelson |
| 6,761,723 B2 | 7/2004 | Buttermann et al. |
| 6,767,367 B1 | 7/2004 | Michelson |
| 6,770,074 B2 | 8/2004 | Michelson |
| 6,773,460 B2 | 8/2004 | Jackson |
| 6,793,679 B2 | 9/2004 | Michelson |
| 6,808,537 B2 | 10/2004 | Michelson |
| 6,814,737 B2 | 11/2004 | Cauthen |
| 6,814,756 B1 | 11/2004 | Michelson |
| 6,827,740 B1 | 12/2004 | Michelson |
| 6,830,570 B1 | 12/2004 | Frey et al. |
| 6,833,006 B2 | 12/2004 | Foley et al. |
| 6,835,208 B2 | 12/2004 | Marchosky |
| 6,849,093 B2 | 2/2005 | Michelson |
| 6,863,673 B2 | 3/2005 | Gerbec et al. |
| 6,893,465 B2 | 5/2005 | Huang |
| 6,902,579 B2 | 6/2005 | Harms et al. |
| 6,908,485 B2 | 6/2005 | Crozet et al. |
| 6,932,844 B2 | 8/2005 | Ralph et al. |
| 6,942,698 B1 | 9/2005 | Jackson |
| 7,048,766 B2 | 5/2006 | Ferree |
| 7,060,073 B2 | 6/2006 | Frey et al. |
| 7,066,960 B1 | 6/2006 | Dickman |
| 7,070,598 B2 | 7/2006 | Lim et al. |
| 7,081,120 B2 | 7/2006 | Li et al. |
| 7,083,650 B2 | 8/2006 | Moskowitz et al. |
| 7,087,055 B2 | 8/2006 | Lim et al. |
| 7,128,760 B2 | 10/2006 | Michelson |
| 7,163,561 B2 | 1/2007 | Michelson |
| 7,179,294 B2 | 2/2007 | Eisermann et al. |
| 7,195,643 B2 | 3/2007 | Jackson |
| 7,204,853 B2 | 4/2007 | Gordon et al. |
| 7,208,014 B2 | 4/2007 | Ralph et al. |
| 7,316,714 B2 | 1/2008 | Gordon et al. |
| 7,318,839 B2 | 1/2008 | Malberg et al. |
| 7,326,251 B2 | 2/2008 | McCombe et al. |
| 2003/0114860 A1 * | 6/2003 | Cavagna et al. ............. 606/104 |
| 2004/0153089 A1 | 8/2004 | Zdeblick et al. |
| 2004/0210313 A1 | 10/2004 | Michelson |
| 2004/0230100 A1 | 11/2004 | Shluzas |
| 2004/0230309 A1 | 11/2004 | DiMauro et al. |
| 2004/0236331 A1 | 11/2004 | Michelson |
| 2004/0249388 A1 | 12/2004 | Michelson |
| 2006/0096275 A1 | 5/2006 | Robel et al. |

FOREIGN PATENT DOCUMENTS

| | | |
|---|---|---|
| FR | 2717068 | 9/1995 |
| WO | WO 01/01895 | 1/2001 |
| WO | WO 02/05733 | 1/2002 |

OTHER PUBLICATIONS

Invitation to Pay Additional Fees pp. 1-4; Annex to Form PCT/ISA 206 pp. 1-3.

B-Twin Expandable Spinal System, web page (http://www.disc-o-tech.com/Articles/Article.asp?CategoryID=4&ArticleID=74, no date given.

Patent Cooperation Treaty, International Search Report, Date completed; Nov. 7, 2006, p. 1-7, ISA, European Patent Office, P.B. 5818 Patentlaan 2 NL—2280 HV Rijswijk.

Patent Cooperation Treaty, International Preliminary Report, Date completed: Dec. 13, 2007, p. 1-20, International Preliminary Examining Authority, European Patent Office—Gitschiner Str. 103 D-10958 Berlin.

Patent Cooperation Treaty, Written Opinion of the International Searching Authority, pg. 1-9, ISA, European Patent Office—Gitschiner Str. 103 D-10958 Berlin.

* cited by examiner

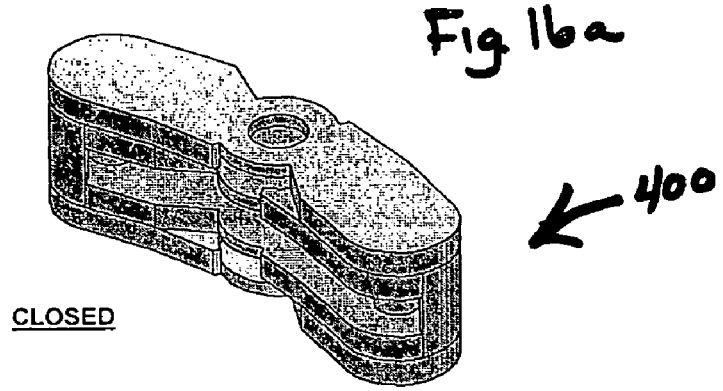
CLOSED
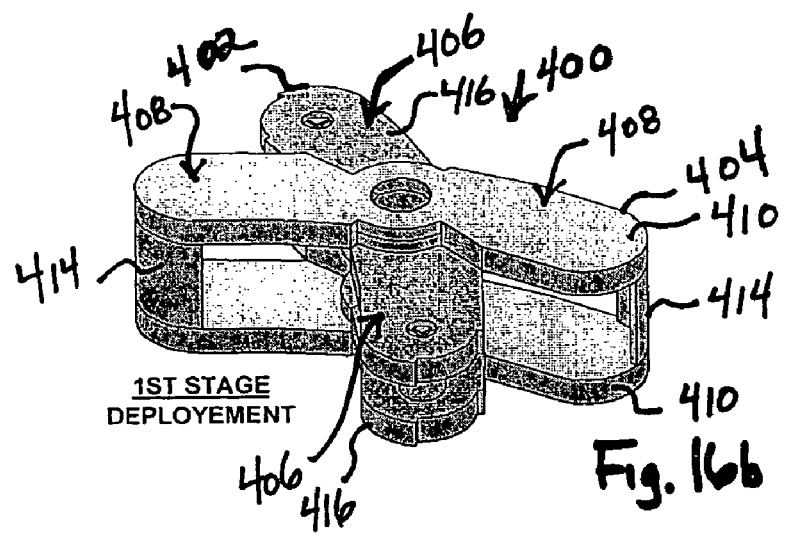
1ST STAGE DEPLOYEMENT
Fig. 16b
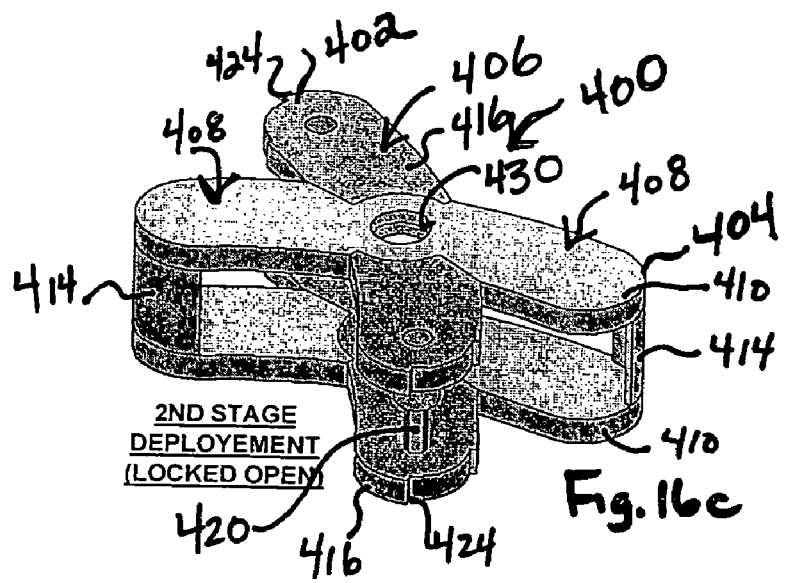
2ND STAGE DEPLOYEMENT (LOCKED OPEN)
Fig. 16c

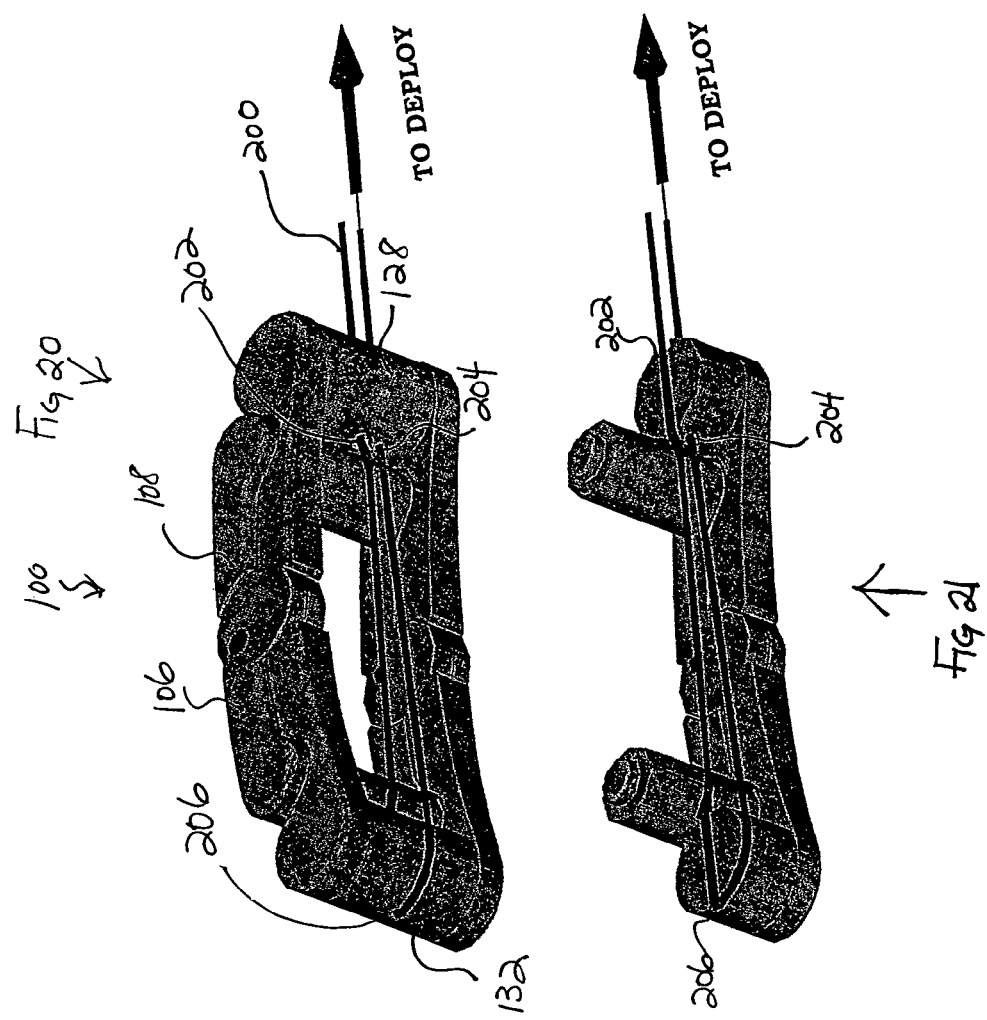

SPINE SURGERY METHOD AND IMPLANT

I. BACKGROUND OF THE INVENTION

A. Field of Invention

This invention pertains to the art of methods and apparatuses regarding spine surgery and more specifically relates to surgical procedures, associated instrumentation and an implant to be positioned within an intradiscal space between two adjacent vertebral bodies.

B. Description of the Related Art

The volume of spinal surgeries to treat degenerative disc and facet disease has steadily increased over the past decade, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have disadvantages. One disadvantage is that the physical components are relatively large and bulky. This reduces surgeon visualization of the surgical site. Another disadvantage of know spinal surgical methods is that known surgical tools and implants are cumbersome and difficult to maneuver within the limited surgical space available.

As a result of the aforementioned disadvantages, many intradiscal "fusion" implants have been developed to replace a degenerative disc and to maintain stability of the disc interspace between adjacent vertebrae until a solid arthrodesis has been achieved. These known "interbody fusion devices" have had variable geometries and have been classified by Zdeblick et al. in U.S. Pat. No. 6,695,851 into two basic categories; solid implants and bony ingrowth implants. Examples of solid implants are provided in U.S. Pat. Nos. 4,878,915, 4,743,256, 4,349,921 and 4,714,469. The previously noted patent to Zdeblick et al. (U.S. Pat. No. 6,695,851) as well as U.S. Pat. No. 4,820,305 to Harms et al. are examples of bony ingrowth implant devices. Other types of implants in the interbody fusion device category are provided in the following U.S. Pat. Nos. 5,397,364 to Kozak; 5,015,247 to Michelson, 4,878,915, 4,743,256, 4,834,757 and 5,192,327 to Brantigan; 4,961,740 and 5,055,104 to Ray; and 4,501,269 to Bagby.

The devices provided in the aforementioned references all have relatively fixed geometries, most commonly rectangular, trapezoidal, or cylindrical in shape. Jackson, in U.S. Pat. No. 6,773,460, has developed anterior interbody device that is expandable relative to the vertical axis of the intradiscal space. Despite this progression in intradiscal implant geometry, a device having an optimized geometry to provide an optimal vertebral endplate footplate is lacking. A specific surgical method and complementary implant instrumentation system is also lacking. Various surgical methods have been devised for the implantation of interbody fusion devices. Dr. Gary Michelson's technique and associated instruments as provided in U.S. Pat. No. 5,484,437 is but one example. These known techniques along with their associated instruments and implants lack one or more of the criteria for optimal use in anterior, posterior, or transforaminal minimally invasive approaches compatible with currently available minimally invasive spine surgery and/or minimal access spinal techniques (MAST).

The present invention provides methods and apparatuses for overcoming these disadvantages by providing an interbody implant that allows for minimally invasive spinal surgery.

II. SUMMARY OF THE INVENTION

According to one aspect of this invention, a method of placing an implant into an intradiscal space between two adjacent vertebral bodies includes the steps of: (1) distracting the intradiscal space between the two adjacent vertebral bodies; (2) inserting the implant into the intradiscal space in a first non-expanded condition having a first effective footprint area $A1$; and, (3) deploying the implant within the intradiscal space to a second expanded condition having a second effective footprint area $A2$ that is greater than $A1$. When in the non-expanded condition, the implant may be passed via commercially available minimal access spinal retractor systems with minimal requirements for bony resection or soft tissue retraction. When in the expanded condition, the implant provides a larger effective footprint area compatible with far more invasive anterior lumbar interbody fusion or bilateral posterior techniques.

According to another aspect of this invention, the implant has a first member and a second member pivotally attached to the first member. With this embodiment, the implant is deployed into the second expanded condition by pivoting the second member with respect to the first member.

According to another aspect of this invention, a cable may be attached to the first or second member. The surgeon may apply tension to the cable and thereby pivot the second member with respect to the first member from the first non-expanded condition to the second expanded condition.

According to another aspect of this invention, when the implant is in the first non-expanded condition, the first member is nested with respect to the second member. This minimizes the size of the implant during insertion within the intradiscal space.

According to another aspect of this invention, the implant can be locked into the second expanded condition to thereby prevent any additional pivoting motion of the first member with respect to the second member. In this locked condition the surgeon can easily make final implant alignment adjustments within the intradiscal space.

According to another aspect of this invention, the locking mechanism can be unlocked thereby enabling the first member to be pivoted with respect to the second member. This permits the surgeon to return the implant to the first non-expanded condition where it can easily be removed from the intradiscal space. This may be necessary, for example, in situations where the surgeon determines that the implant should be replaced.

According to still another aspect of this invention, an implant has a first contact surface adapted to contact a first vertebral body and a second contact surface adapted to contact a second vertebral body adjacent the first vertebral body. The implant is selectively deployable, when positioned within an intradiscal space between the first and second vertebral bodies, from a first non-expanded condition where the first contact surface has a first effective footprint area $A1$ to a second expanded condition where the first contact surface has a second effective footprint area $A2$ that is greater than $A1$.

According to another aspect of this invention, the implant has a first member and a second member that is selectively pivotal with respect to the first member from the first non-expanded condition to the second expanded condition. The first member may have first and second beams each having outer surfaces and the second member may also have first and second beams each having outer surfaces. The outer surface of the first beam of the first member and the outer surface of the first beam of the second member may define the first contact surface. Similarly, the outer surface of the second beam of the first member and the outer surface of the second beam of the second member may define the second contact surface.

According to another aspect of this invention, a pair of posts may connect the first and second beams of the first member together and a separate pair of posts may similarly connect the first and second beams of the second member together. In one embodiment, these posts are positioned on the outer ends of the first and second members. This provides maximum compression strength at the outer interfaces of the implant to more closely approximate surface contact with the concavity of the bony vertebral body endplates.

According to another aspect of this invention, the implant has a locking mechanism for locking the position of the second member with respect to the first member and thereby locking the implant in the second expanded condition. In one embodiment, the locking mechanism includes: (a) a pin positioned in the first beam of the first member; (b) a spring that urges the pin away from the first member; and, (c) an opening formed in first beam of the second member. When the implant is placed into the second expanded condition, the pin is aligned with the opening and the spring forces the pin into the opening to thereby lock the implant in the expanded condition.

According to another aspect of this invention, if necessary, the pin can be sheared to unlock the locking mechanism. In one embodiment, the pin has a channel permitting the pin to be sheared at the interface of the first beam of the first member and the first beam of the second member. With this arrangement, both portions of the sheared pin remain confined within the implant and thus will not be inadvertently left within the intradiscal space.

One advantage of this invention is that the implant has an open profile when fully expanded, maximizing boney ingrowth surface area and bone graft-host contact.

Another advantage of this invention is that the surgeon achieves enhanced visualization of the bone graft-vertebral body endplate interface.

Another advantage of this invention is that the implant allows for minimally invasive deployment via either an anterior, posterior or anterolateral surgical approach.

Another advantage of this invention is that the implant can be used as an interbody fusion device or as a motion-preservation device, either constrained or unconstrained.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein:

FIG. 16a shows an alternate embodiment implant in a non-expanded, non-deployed condition.

FIG. 16b shows the implant of FIG. 16a in a first stage of deployment.

FIG. 16c shows the implant of FIGS. 16a and 16b in the expanded, fully deployed condition.

FIG. 20 is a side perspective view of the implant in the non-expanded, non-deployed condition similar to that shown in FIG. 2 but showing the cable that may be used to deploy the implant.

FIG. 21 is a view similar to that shown in FIG. 20 but with the top beams removed to show how the cable is received within the posts.

IV. DETAILED DESCRIPTION OF INVENTION

Figure 1:
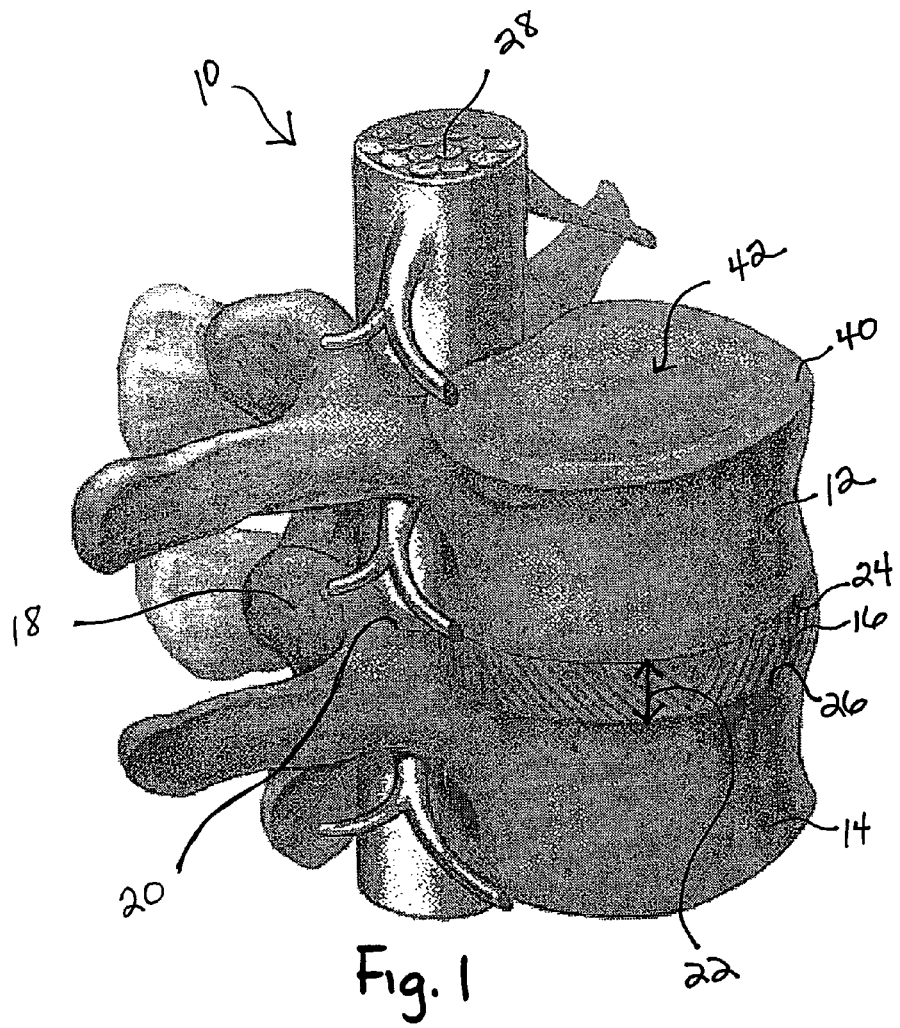
FIG. 1 is a side perspective view of a spinal segment.

Referring now to the drawings wherein the showings are for purposes of illustrating one or more embodiments of the invention only and not for purposes of limiting the same, FIG. 1 shows a portion of a spinal column, a spinal segment 10 that may use the implant 100 (shown in FIGS. 2-5) of this invention. The spinal segment 10 is made up of two vertebrae 12, 14 attached together by ligaments with a disc 16 separating them. Facet joints 18 fit between the two vertebrae 12, 14 and allow for movement. The neural foramen 20 between the vertebrae 12, 14 allow space for the nerve roots to travel freely from the spinal cord 28 to the body. The disc 16 occupies the intradiscal space 22. By intradiscal space 22 it is meant the space usually occupied by the disc 16 between two adjacent vertebral bodies 12, 14 and more specifically the space 22 between adjacent endplates 24, 26 of the vertebral bodies 12, 14 as shown. As the components and operation of a spinal column is well known to those of skill in the art, further detail will not be provided here.

Figure 2:
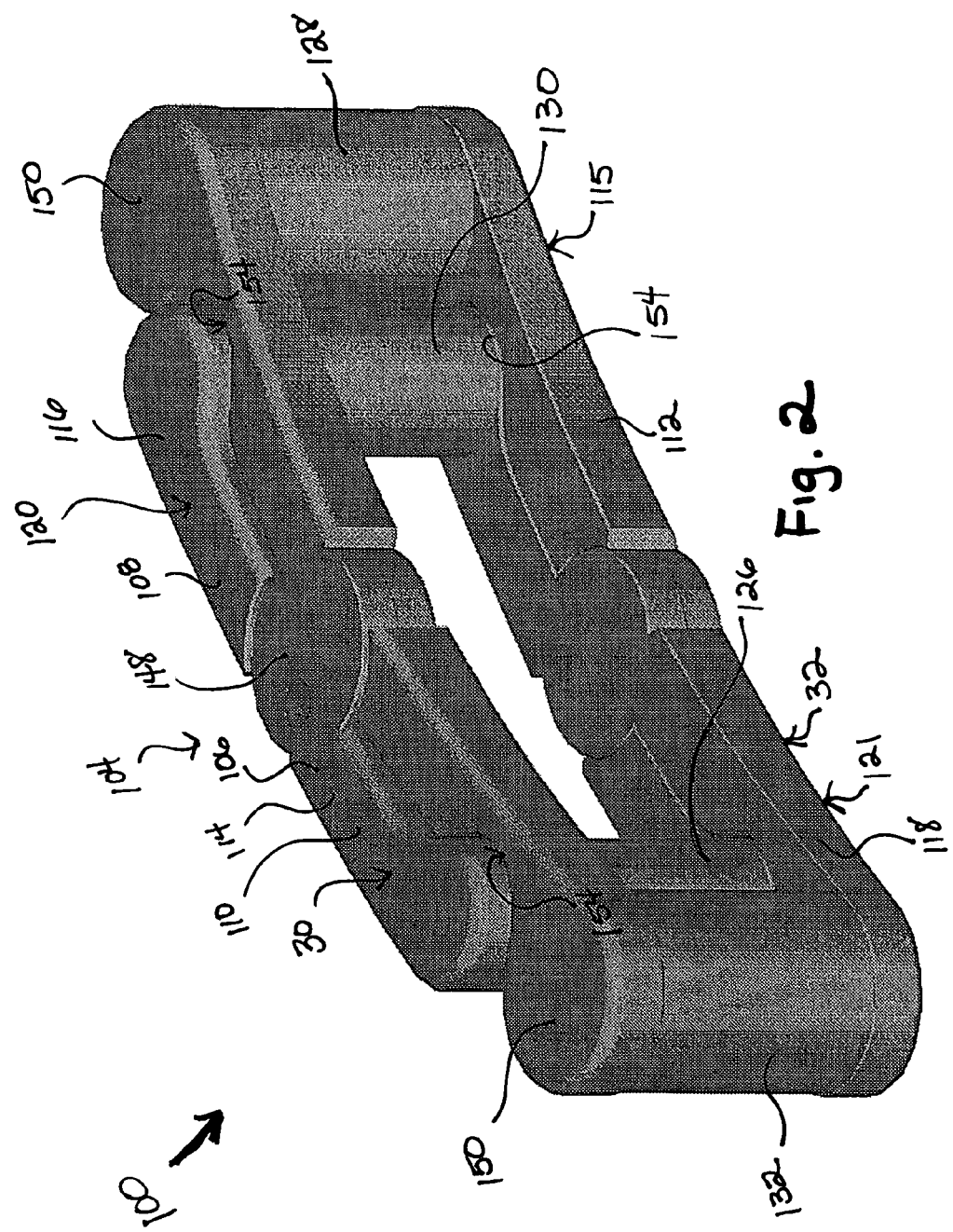
FIG. 2 is a side perspective view of the implant of this invention in the non-expanded, non-deployed condition.
Figure 4:
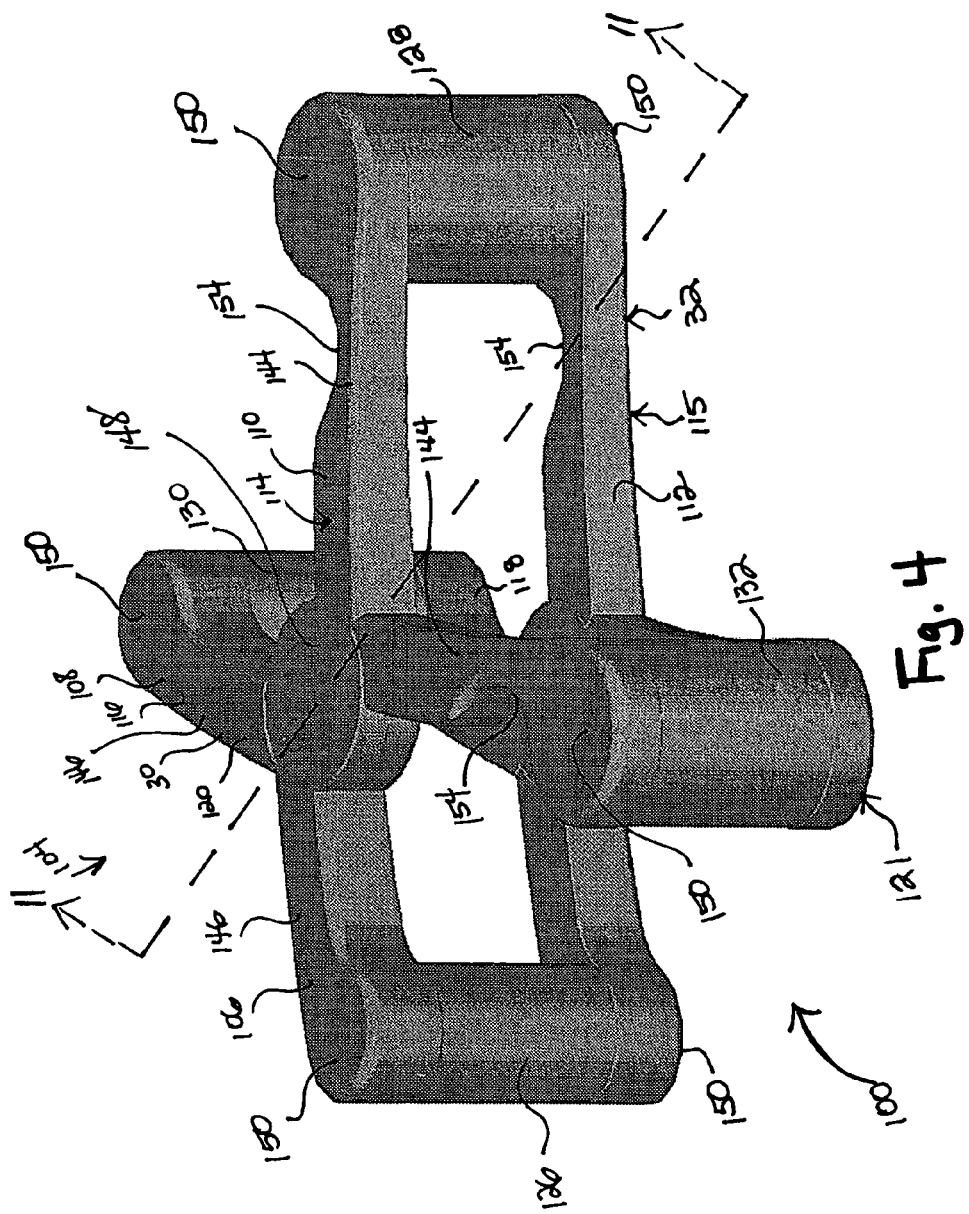
FIG. 4 is a perspective side view of the implant shown in FIGS. 2 and 3 but in the expanded, deployed condition.
Figure 5:
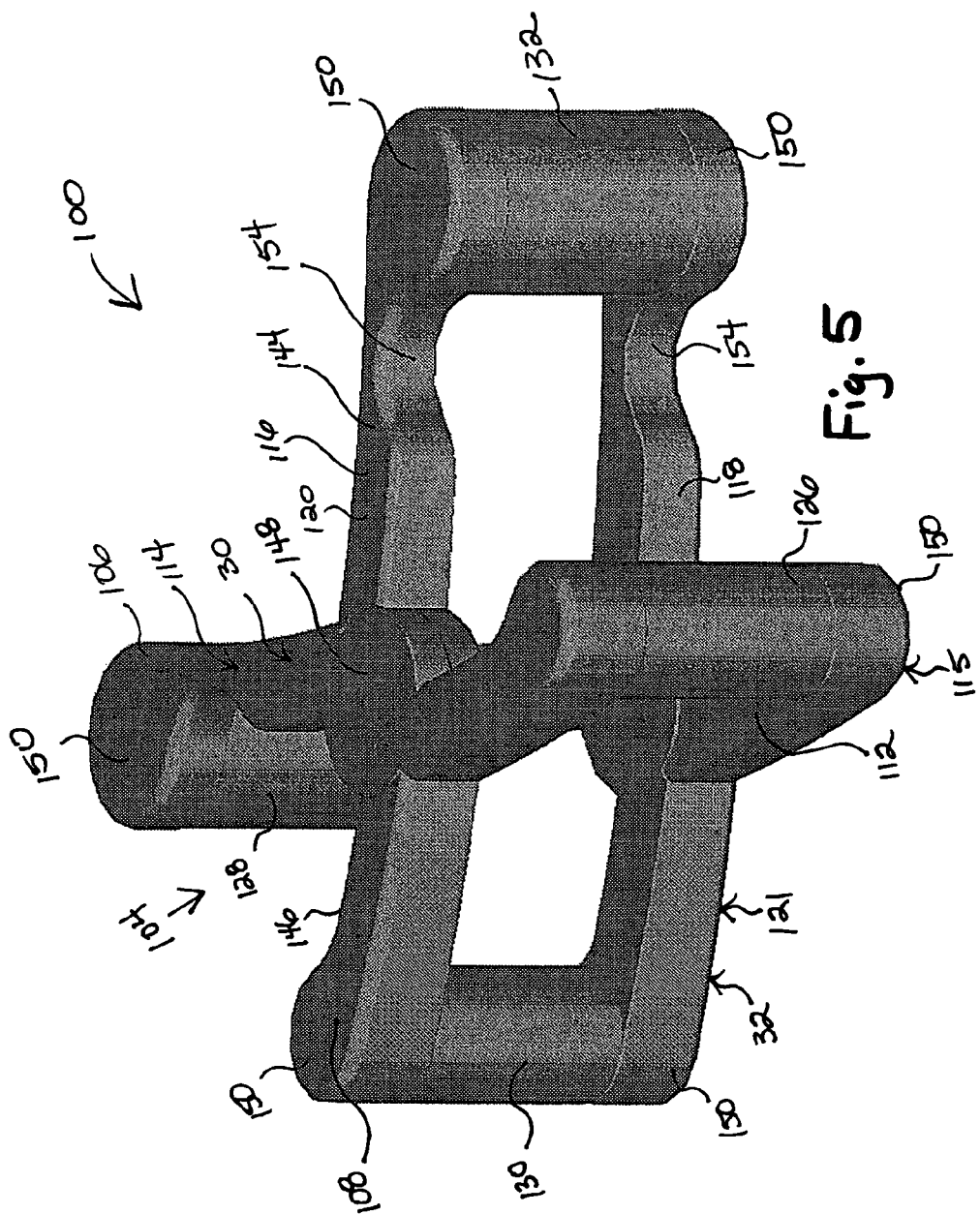
FIG. 5 is a view similar to that shown in FIG. 4, but from another side.

With reference now to FIGS. 1, 2 and 4, the implant 100 can be positioned within the intradiscal space 22 in a first non-expanded condition, as shown in FIG. 2, and can then be deployed within the intradiscal space 22 to a second expanded condition, as shown in FIG. 4. This expandable design is very beneficial for the surgeon. When in the non-expanded reduced footprint condition, the implant 100 is small enough to be passed through a standard microdiscectomy type annulotomy, making it truly compatible with minimally invasive surgical (MIS) techniques. Commercially available minimal access spinal retractor systems can be used with minimal requirements for bony resection or soft tissue retraction. Once placed within the intradiscal space 22, the implant 100 can be deployed into the expanded condition where it provides a larger effective footprint area. This larger footprint is compatible with more invasive anterior lumbar interbody fusion or bilateral posterior techniques.

Figure 6:
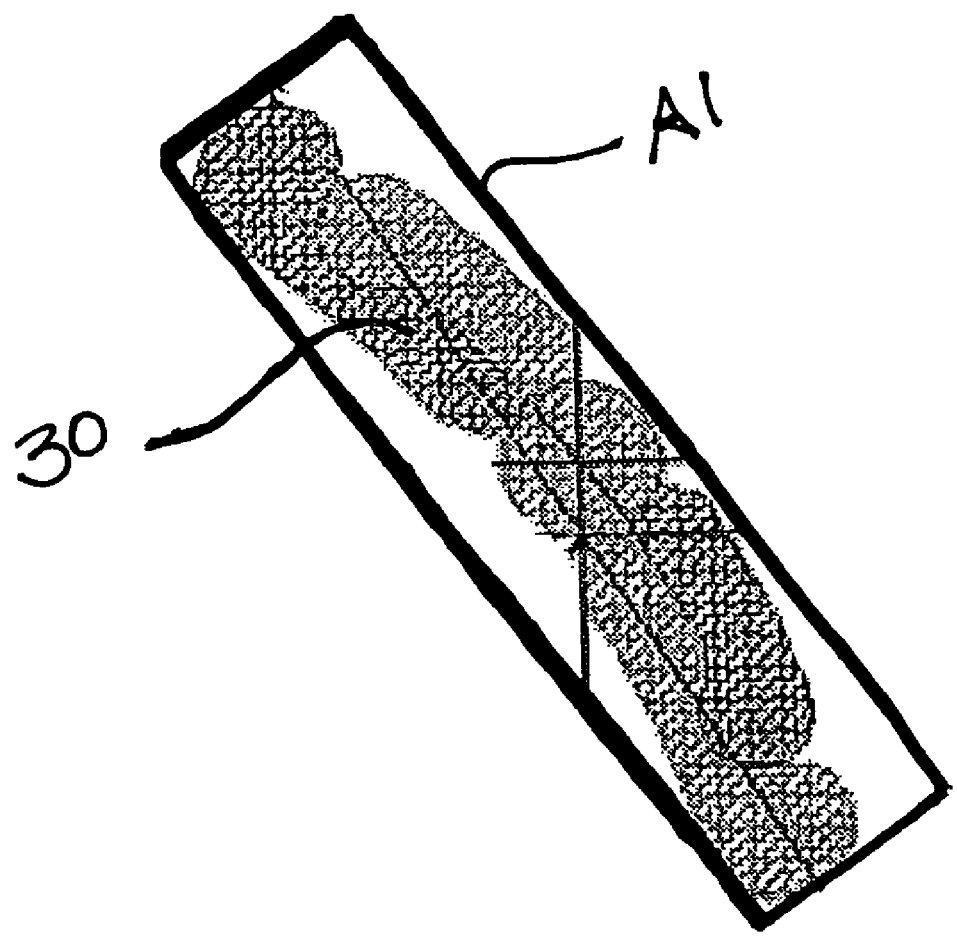
FIG. 6 is a top view illustrating the effective footprint area of the implant when in the non-expanded condition.
Figure 7:
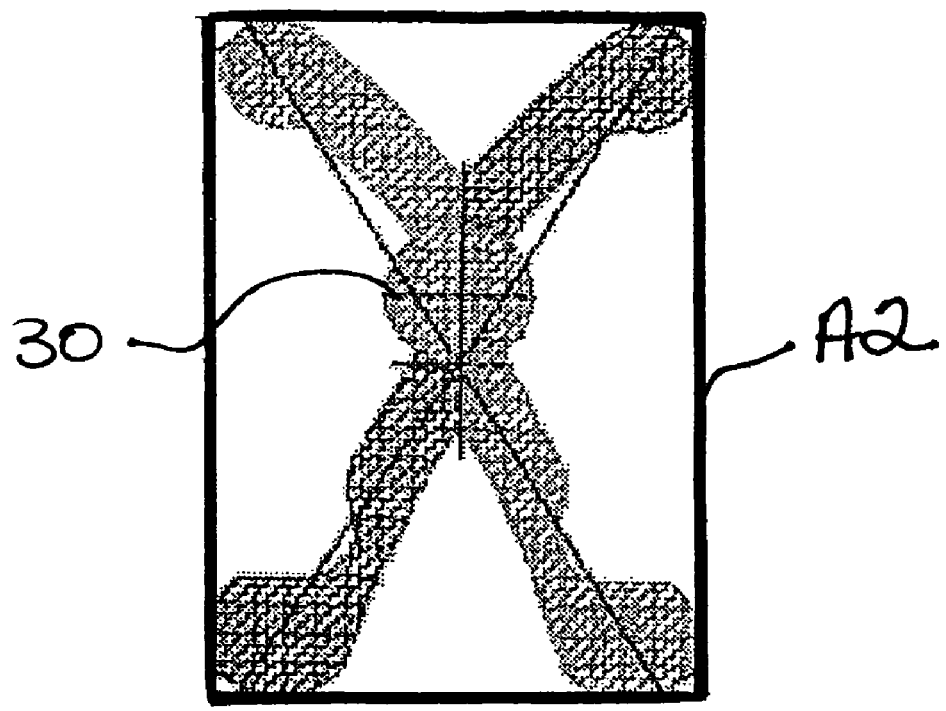
FIG. 7 is a top view similar to that of FIG. 6 but illustrating the effective footprint area of the implant when in the expanded, deployed condition.

With reference now to FIGS. 1-7, the implant 100 has a first vertebral body endplate contact surface 30 that provides a first effective footprint area A1, as illustrated in FIG. 6, when in the first non-expanded condition. The first endplate contact surface 30 provides a second effective footprint area A2, as illustrated in FIG. 7, when in the second expanded condition. For purposes of this patent, "effective footprint area" is defined as the area of the smallest rectangle that would encompass or surround the implant vertebral contact surface 30, where the rectangle perimeter contacts the implant 100 contact surface 30 perimeter at a minimum of two points. By "smallest rectangle" it is meant the rectangle having the smallest possible area. Thus, for example, if the implant contact surface 30 was rectangular in shape with a width W and a length L, the effective footprint area would be the area of a rectangle with width W and length L (the effective footprint area would be W times L). If, as another example, the implant contact surface 30 was circular in shape with a diameter D, the effective footprint area would be the area of a square with sides having a length D (the effective footprint area would be D times D). As a general rule, the larger this ratio the easier for the surgeon to place the implant 100 into position while still providing excellent contact with the adjacent vertebrae endplates 24, 26. It is preferred that the ratio A2/A1 is at least 1.05. More preferably, the ratio A2/A1 is at least 1.3 and most preferably the ratio A2/A1 is at least 1.5. For the implant 100 embodiment shown in FIGS. 2-7, the ratio of the second effective foot print area A2 to the first effective foot print area A1, A2/A1 is approximately 1.8.

With reference now to FIGS. 1-5, the implant 100 may not only have the first vertebral body endplate contact surface 30 adapted to contact the first vertebral body endplate 24 but also may have a second vertebral body endplate contact surface 32 adapted to contact the second vertebral body endplate 26. Each of the first and second contact surfaces 30, 32 may expand simultaneously from the first effective footprint areas A1 to the second effective footprint areas A2. However, it is also contemplated to only expand one of the contact surfaces 30, 32. The implant 100 may have a first member 106, a second member 108 and a pivotal connection 104 between the first and second members 106, 108. As a result, the second member 108 can be pivoted with respect to the first member 106 from the first non-expanded condition to the second expanded condition. In the embodiment shown, the first member 106 has first and second beams 110, 112 each having outer surfaces 114, 115. Similarly, the second member 108 has first and second beams 116, 118 each having outer surfaces 120, 121. The outer surface 114 of the first beam 110 of the first member 106 and the outer surface 120 of the first beam 116 of the second member 108 define the first contact surface 30. Similarly, the outer surface 115 of the second beam 112 of the first member 106 and the outer surface 121 of the second beam 118 of the second member 108 define the second contact surface 32. These contact surfaces 30, 32 are preferably serrated/knurled to facilitate cutting into bony endplates to prevent rotation or expulsion of the device by external rotational or flexion-extension forces.

With reference now to FIGS. 1-5 and 18, the implant 100 may have first and second posts 126, 128 connecting the first beam 110 of the first member 106 to the second beam 112. Similarly, third and fourth posts 130, 132 may connect the first and second beams 116, 118 of the second member 108. These posts 126, 128, 130, 132 may attach to the beams 110, 112, 116, 118 in any manner chosen with sound engineering judgment. In one embodiment shown in FIG. 18, however, each post 126, 128, 130, 132 has a dowel member 134 extending from at least one end and preferably each end. These dowels 134 may be received in openings 135 provided on the inner surfaces 136 of the beams 110, 112, 116, 118. This provides for a secure connection and makes the use of fasteners and adhesives unnecessary. In the embodiment shown, the dowels 134 have a polygonal shape that matches the polygonal shape of the openings 135. This type of connection prevents the posts from rotating with respect to the beams. In another embodiment, the dowels 134 and openings 135 are circular in shape to permit the dowels 134 to rotate within the openings 135. The particular shape of the dowels 134 and openings 135 can be selected based on sound engineering judgment. In the embodiment shown, each post 126, 128, 130, 132 is positioned at the outer ends of each beam 110, 112, 116, 118. This may be preferred because this provides maximum compression loading characteristics at the area most likely to carry such a load; namely, with reference to FIG. 1, at the outer rim 40 of each vertebrae endplate 42. It should be noted, however, that depending on the particular use, the number of posts used and their positions can be varied in accordance with the load requirements across the beams and sound engineering principles. In another embodiment, one or more washer members (not shown), having openings that receive the dowels 134, may be used to extend the height of an individual post for a specific surgical need.

Figure 3:
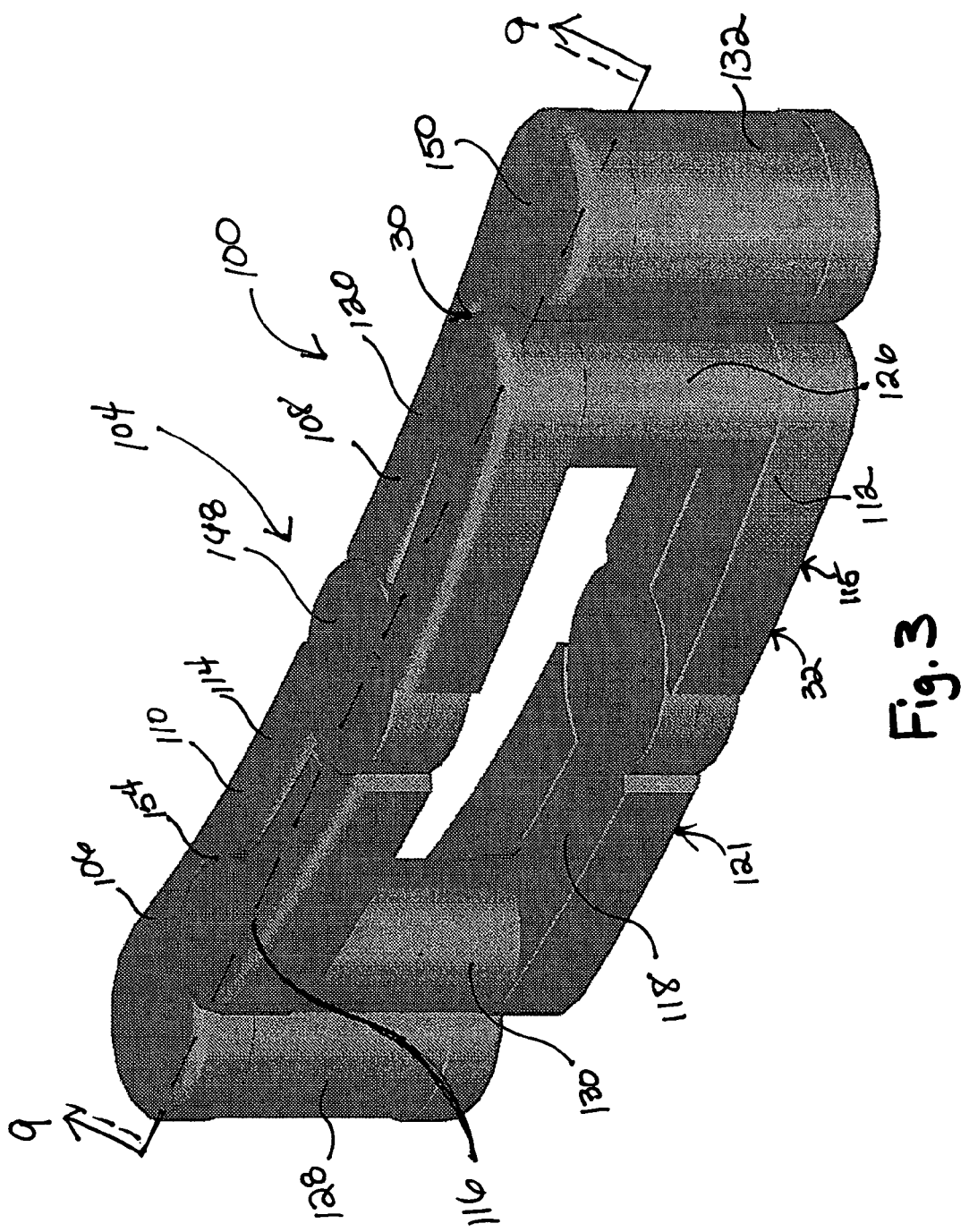
FIG. 3 is a view similar to that shown in FIG. 2, but from the opposite side.
Figure 19:
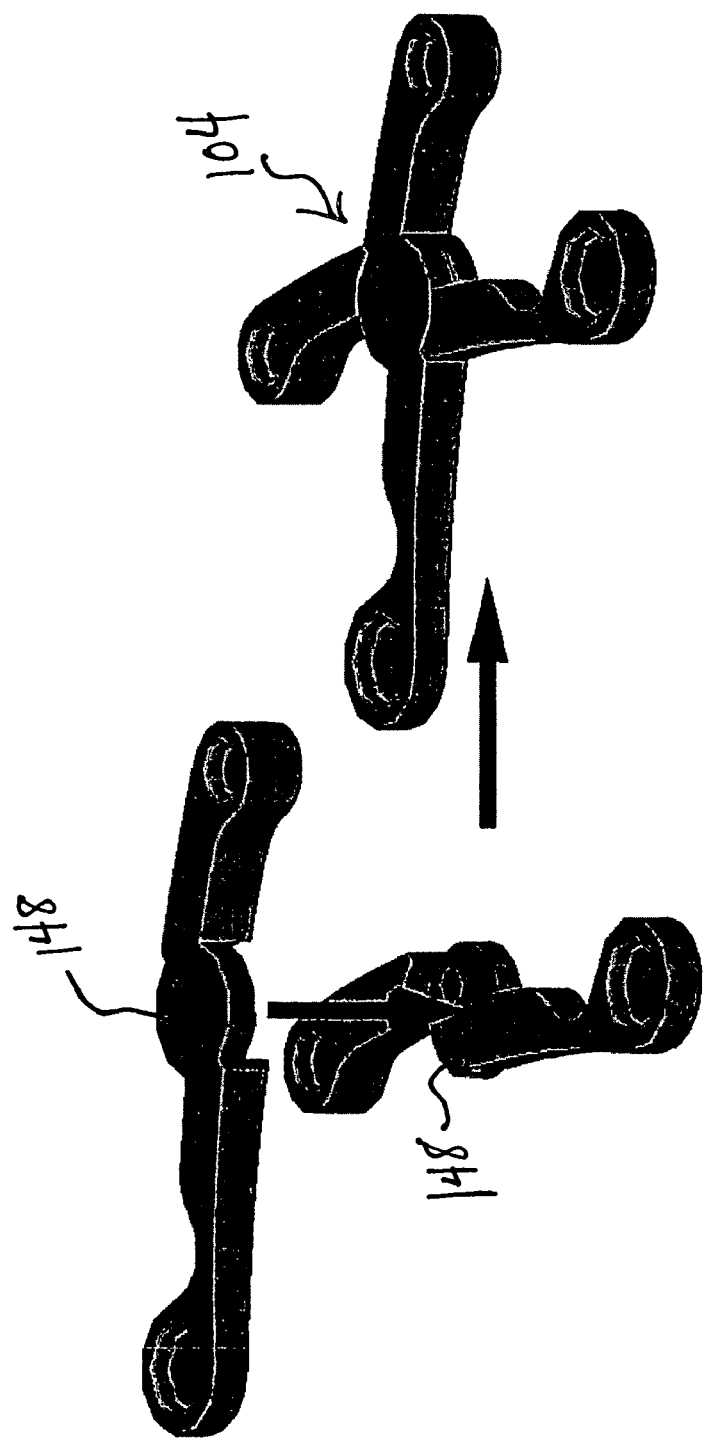
FIG. 19 is an assembly drawing illustrating one embodiment of how the mid-portion of one beam may be juxtaposed to the mid-portion of another beam to form a pivotal connection.

With reference to FIGS. 1-5, each beam may have first and second limbs 144, 146 extending from a mid-portion 148. Preferably, pods 150 are defined at the ends of each limb 144, 146. The pods 150 may be flared relative to the width of the limbs 144, 146. They are also bulbous with the ends being tapered with a chamfer type profile to facilitate advancement and deployment of the implant 100 within the intradiscal space 22 and to match the anatomical concave rim 40 of a typical vertebral body endplate 42 shown in FIG. 1. Preferably, each beam has one limb 144 that is longer than the opposite limb 146. More preferably, the extra length is equal to the width of a single pod 150, as shown. The longer limb 144 preferably has a groove 154 that receives the pod 150 in the opposite beam, as shown. This design provides for easy nesting of the first and second members 106, 108 as shown in FIGS. 2 and 3. This nesting minimizes the overall width of the implant 100 and, thus, is advantageous when inserting the implant 100 into the intradiscal space 22, yet permits maximal surface area to the pods 150. Note that the tapered pods 150 are most likely the primary portions of the implant 100 that bear the axial, compressive loading. In one embodiment, the mid-portions 148 of each beam may have a circular cross-section, as shown. Juxtaposing the circular mid-portion 148 of one beam 110 with the adjacent beam 116, as illustrated in FIG. 19, creates the preferred pivotal connection 104. This pivotal connection 104 provides for easy manipulation of the implant 100 from the first non-expanded condition into the deployed, expanded condition. This arrangement also makes additional fasteners, pivot pins, bearings and the like unnecessary. This provides for an implant that is easy to manufacture and easy to deploy. The first member 106 may be substantially parallel to the second member 108 when the implant 100 is in the first non-expanded condition. This minimizes the space requirements for the implant 100. Preferably, the first and second members 106, 108 are curvilinear in shape, as shown. This curvilinear shape provides procedural options for the surgeon. The surgeon may, for example, use a vertically oriented posterior lumbar interbody fusion technique (PLIF) or may use a transforaminal interbody fusion technique (TLIF). The particular radii of curvature can be selected based on preoperative and intraoperative templating.

Figure 9:
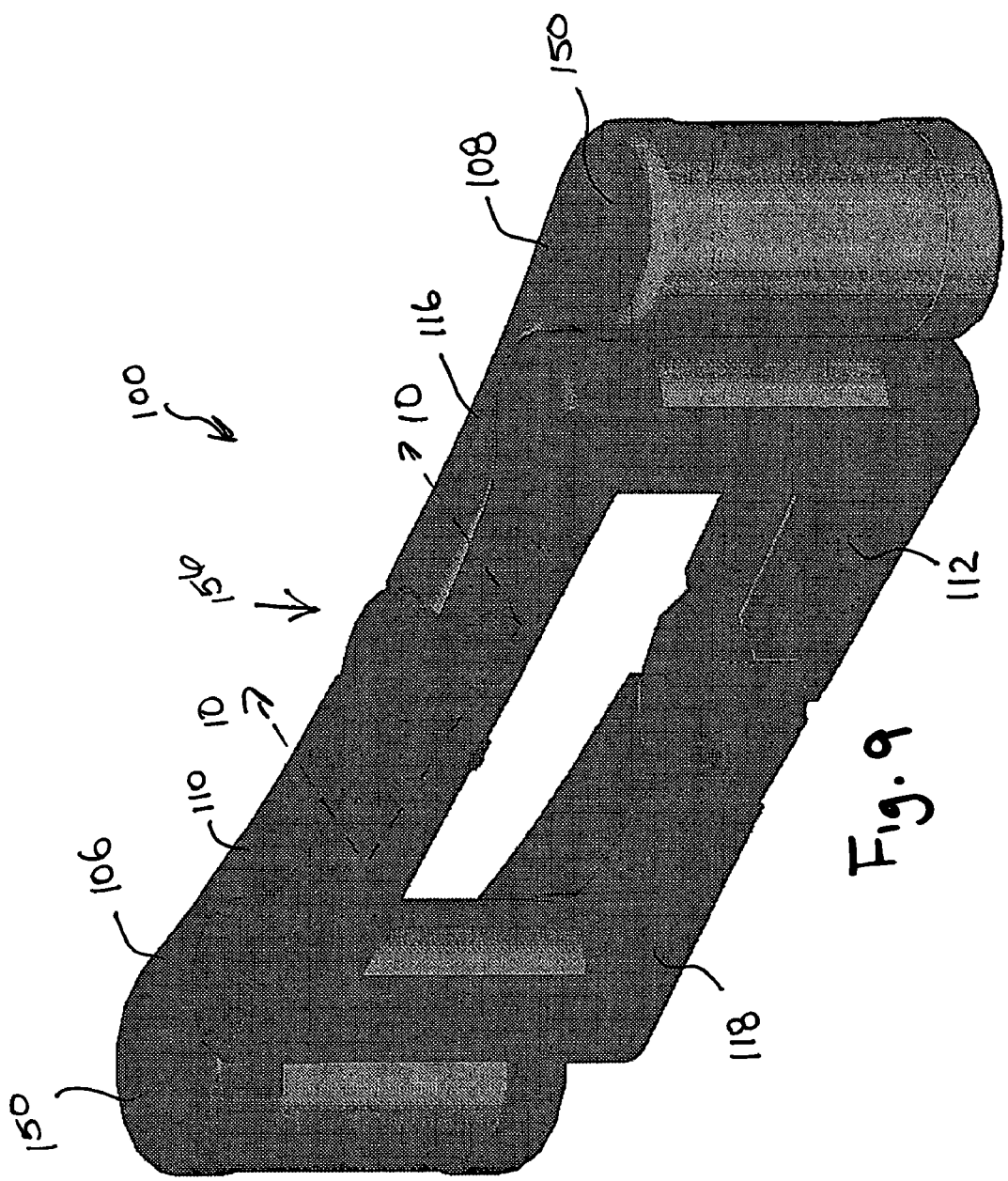
FIG. 9 is a sectional view taken along the line 9-9 of FIG. 3 illustrating the locking mechanism in an unlocked condition.
Figure 10:
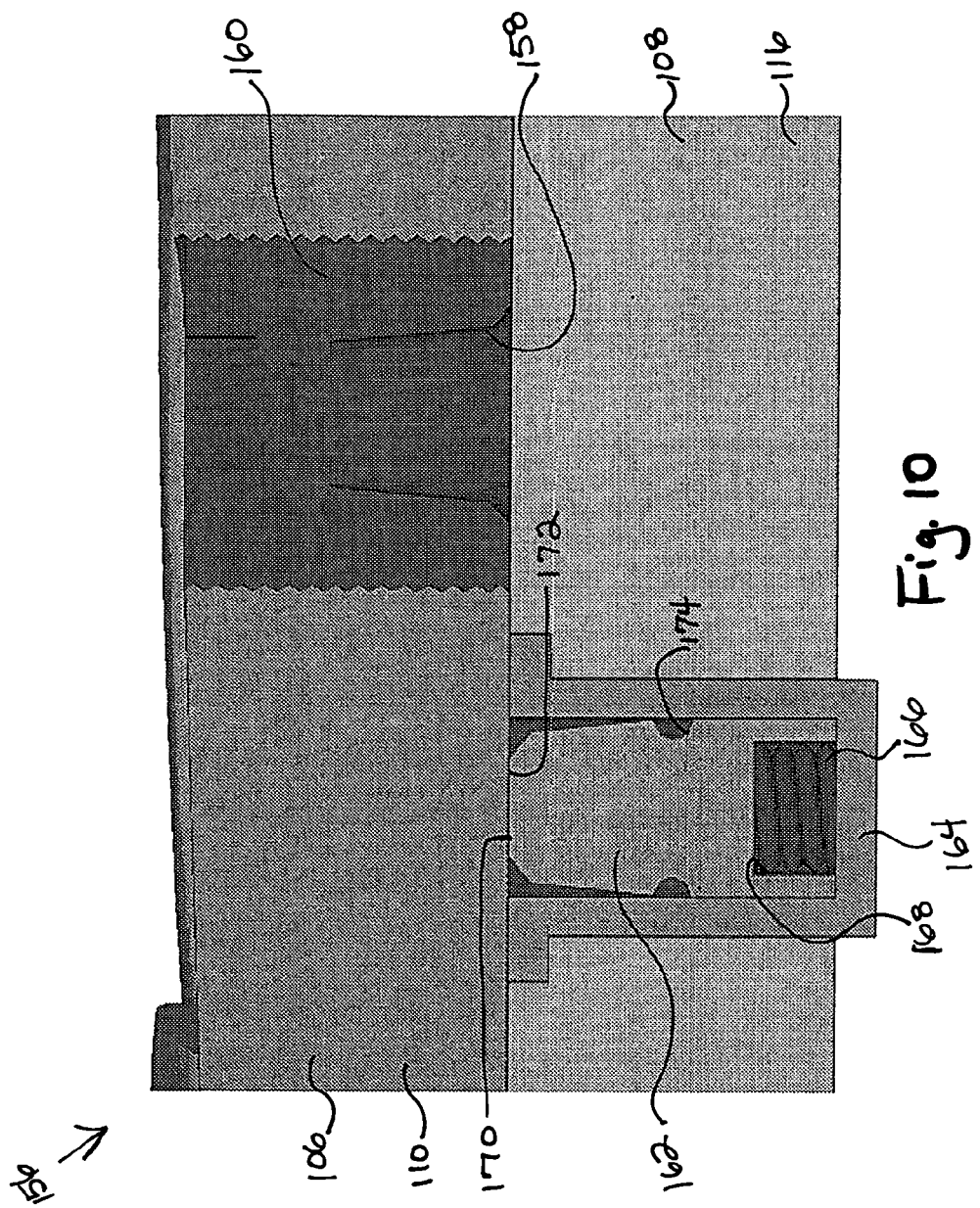
FIG. 10 is an exploded view taken along the lines 10-10 of FIG. 9 and illustrating more details of the locking mechanism.
Figure 11:
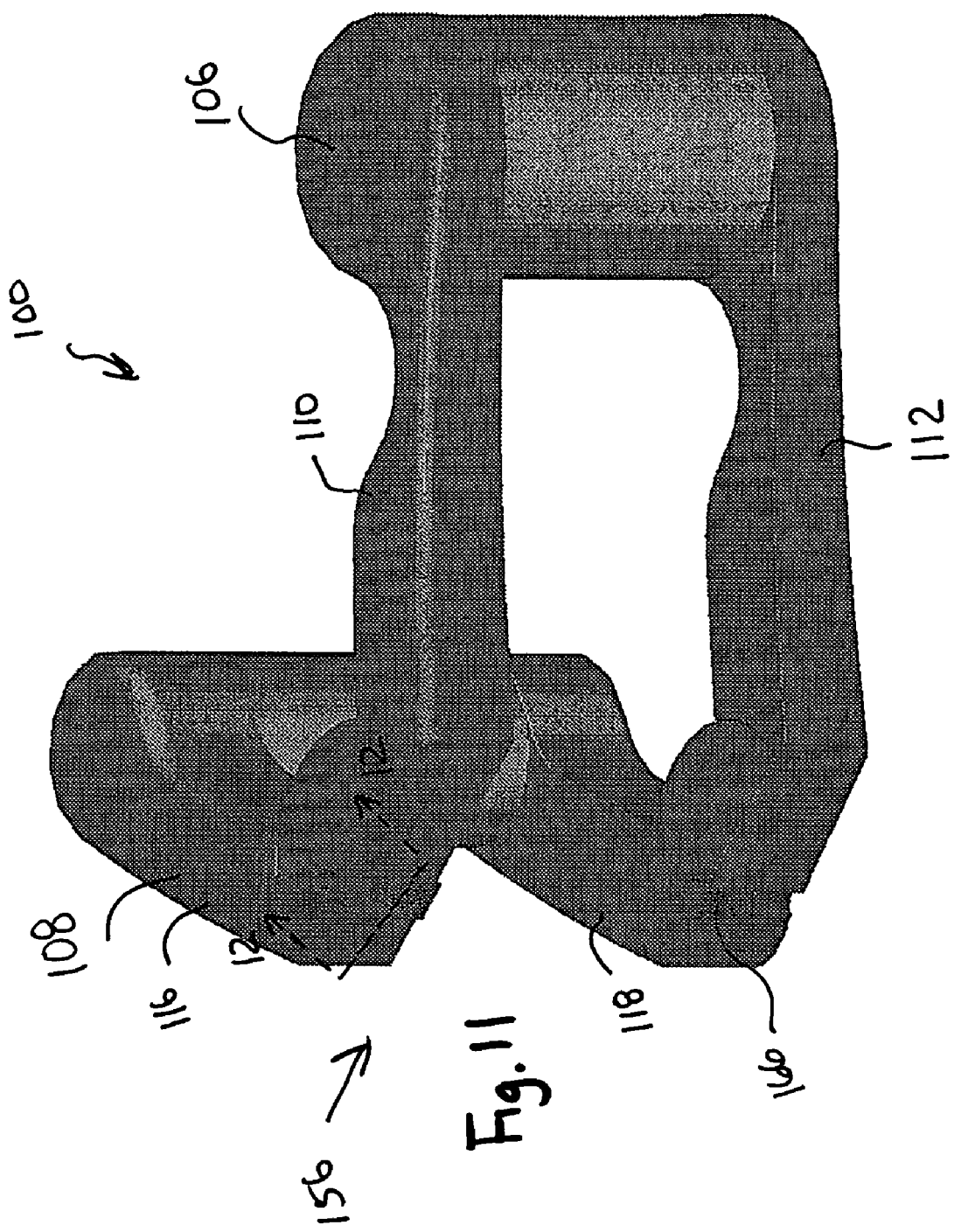
FIG. 11 is a sectional view taken along the line 11-11 from FIG. 4 and illustrating the locking mechanism in a locked condition.
Figure 12:
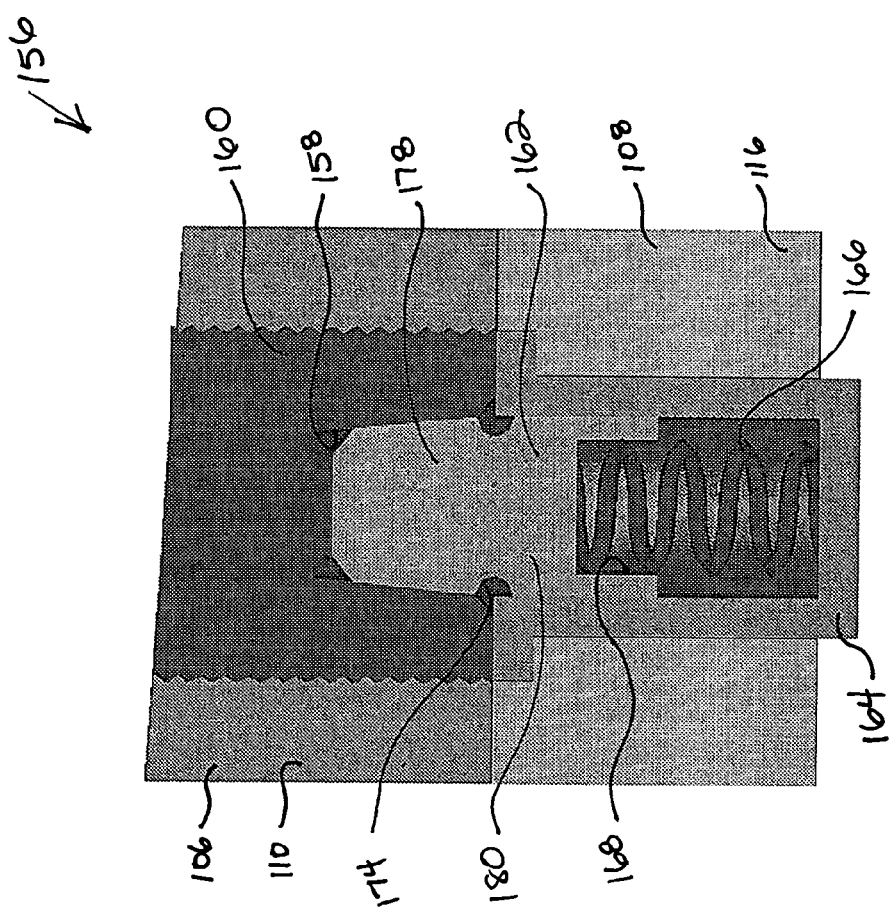
FIG. 12 is an exploded view taken along the lines 12-12 in FIG. 11 and illustrating more details of the locking mechanism in the locked condition.

With reference now to FIGS. 9-12, a locking mechanism 156 may be used to lock the position of the second member 108 with respect to the first member 106 and thereby lock the implant 100 in the second expanded condition. While the particular design for the locking mechanism 156 can be any chosen with sound engineering judgment, in the embodiment shown a first opening 158 is formed in the first beam 110 of the first member 106. This opening can be formed in any manner chosen with sound engineering judgment. For the embodiment shown, a threaded plug 160 is received in the beam 110 and contains the first opening 158. A first pin 162 may be positioned in the first beam 116 of the second member 108. This pin 162 may also be positioned within the second member 108 in any well chosen manner. In the embodiment shown, a generally cylindrical cup portion 164 is received within the second member 108. Within the cup portion 164 a biasing means, preferably a spring 166, is positioned as shown. The pin 162 has a chamber 168 that receives the spring 166. As shown, the pin 162 when fully received within the cup 164 compresses the spring 166 and the pin's upper surface 170 contacts the inner surface 172 of the first member 106. In this way, when in the unlocked condition, the pin 162 is held in place within the cup member 164. As can be seen in FIGS. 9 and 10, the pin 162 and the opening 158 are not in axial alignment when the implant 100 is in the non-expanded condition. In fact, they intentionally are held out of alignment through the pivoting action from the non-expanded condition until the fully expanded condition or fully deployment is reached. This is shown in FIGS. 11 and 12. In this position, the pin 162 is aligned with the opening 158 and thus the biasing force from the spring 166 forces the pin 162 into the opening 158. It should be noted that this insertion of the pin 162 into the opening 158 occurs automatically when the second member 108 is pivoted relative to the first member 106 to a predetermined degree. The particular degree can be varied depending on the needs of the surgeon. Once the pivoting angle is reached, the pin is received within the opening 158 as shown in FIG. 12. In this condition, the second member 108 cannot be pivoted relative to the first member 106.

With continuing reference to FIGS. 9-12, in the event that the surgeon needs to replace the implant 100 or otherwise remove it, it is necessary to return the implant 100 back to the non-expanded condition. To accomplish this, note that the first pin 162 can be broken, and more preferably sheared, into two pieces so that the first and second members 106, 108 can be pivoted back to the non-expanded condition. In the embodiment shown, the pin 162 has a channel 174. As seen best in FIG. 12, this channel 174 is formed in the outer surface of the pin 162 and is axially positioned such that its center is coplanar with the interface of the first and second member 106, 108. As a result of this design, should the surgeon need to unlock the locking mechanism 156 the surgeon need only exert sufficient force on the pin 162 to shear it at the channel 174. Note that the depth of the channel 174 can be varied to vary the torque required to shear the pin 162. Note also that this design provides that upon shearing of the pin 162, the top portion 178 of the pin 162 remains in the opening 158 while the bottom portion 180 of the pin 162 remains in the cup member 164. As a result, both portions of the sheared pin 162 remain confined within the implant 100 and thus will not be inadvertently left within the intradiscal space 22 when the implant 100 is removed.

With reference to FIGS. 2 and 4, the method used by the surgeon to deploy the implant 100 can be any that permits the surgeon to pivot the first member 106 with respect to the second member 108 within the limited intradiscal space 22. In one embodiment, the surgeon can use a conventional inserter and/or distractor (neither tool shown) to deploy the implant 100. In another embodiment, shown in FIGS. 20-23, a cable 200 may be used to deploy the implant 100. The cable 200 may extend between a post on the first member 106 and a post on the second member 108. For the embodiment shown, the second post 128 of the first member 106 has first and second cable cavities 202, 204 and the fourth post 132 of the second member 108 has a third cable cavity 206. The first cable cavity 202 may be positioned above the second cable cavity 204 along the axis of the second post 128 as shown. The cable 200 may include an enlarged section 210 with an outer diameter greater than the diameter of the third cable cavity 206 yet smaller than the diameter of the first cable cavity 202 for reasons to be discussed below. The cable 200 may be inserted within the cable cavities as shown with the enlarged section 210 positioned between the first cable cavity 202 and the third cable cavity 206.

Figure 22:
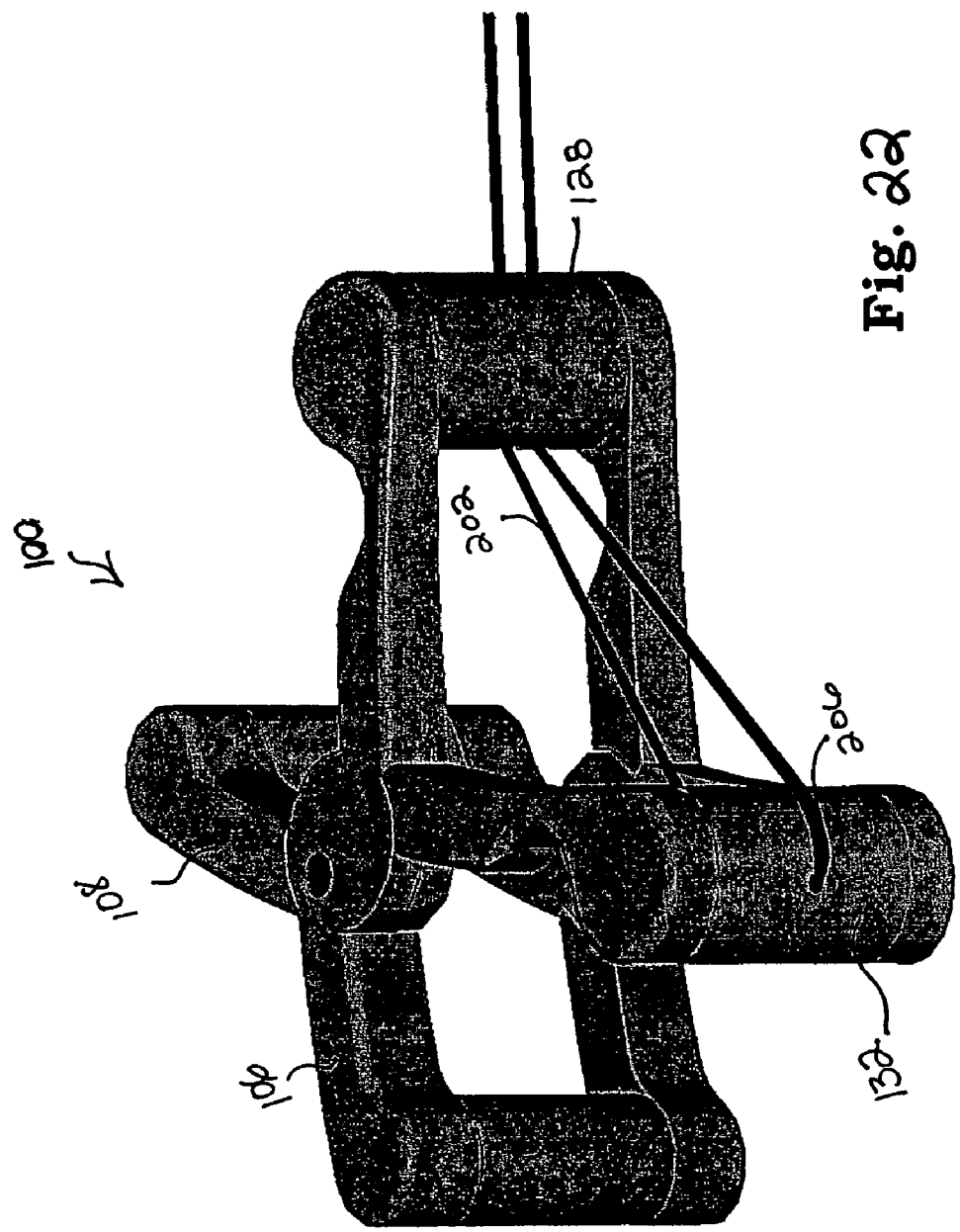
FIG. 22 is a view similar to that shown in FIG. 20 but with the implant in the deployed condition.
Figure 23:
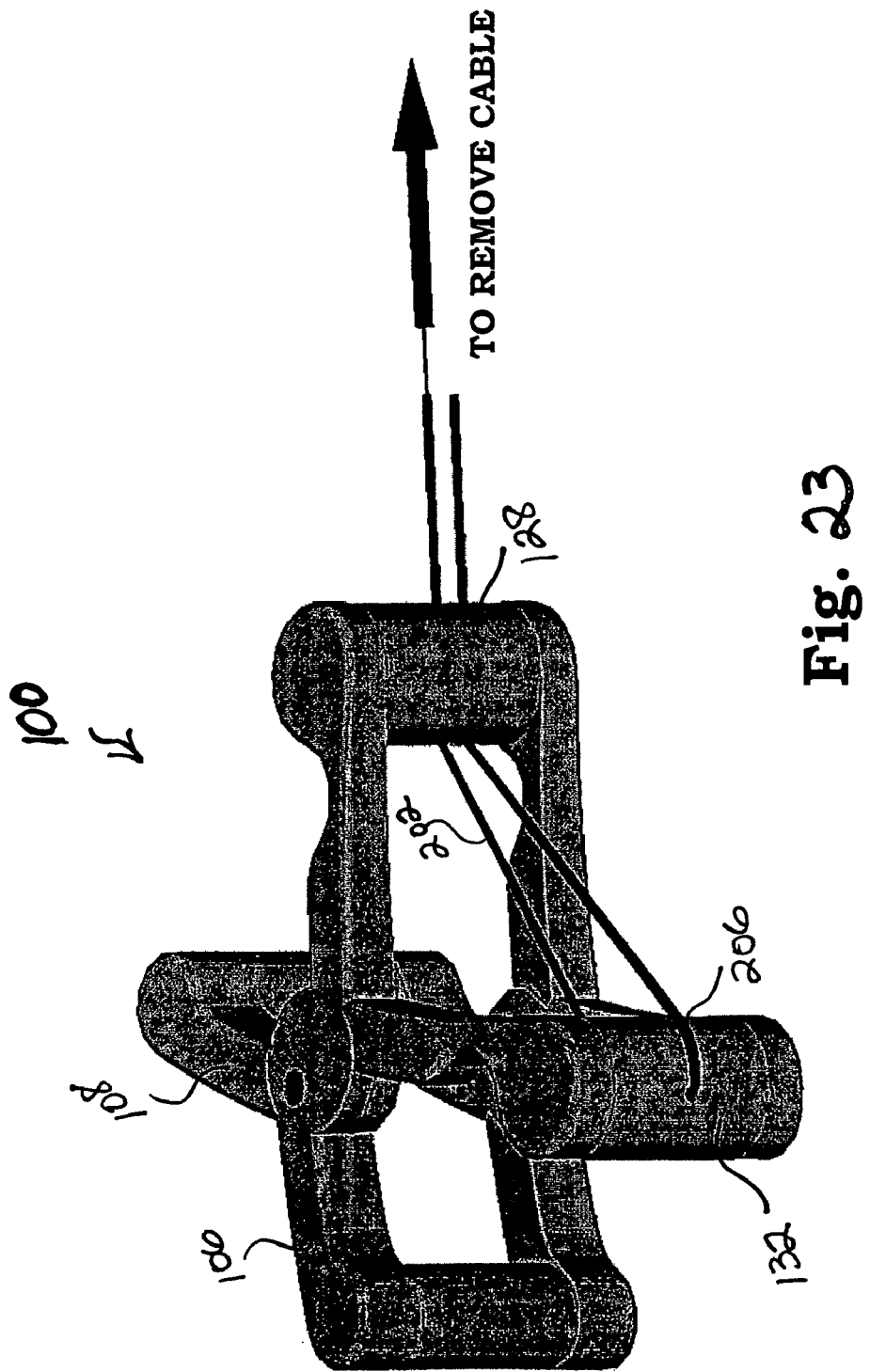
FIG. 23 is a perspective view similar to that shown in FIG. 22 but illustrating how the cable can be removed.

With continuing reference to FIGS. 20-23, deployment of the implant 100 from the first non-expanded condition, shown in FIG. 20, to the second expanded condition, shown in FIG. 22, will now be described. All the surgeon needs to do is apply tension to the cable 200 as indicated by the arrows in FIGS. 20 and 21. This tension begins to pull the cable 200 through the second and third cable cavities 204, 206. Linear motion of the cable 200 soon stops, however, because the enlarged section 210 engages the third cable cavity 206 due to the difference in diameter noted above. At this point, continued application of tension to the cable 200 causes the second member 108 to pivot with respect to the first member 106 and thus causes the implant 100 achieve the expanded condition, shown in FIG. 22. After deployment of the implant 100, the surgeon may, if necessary, apply additional tension to the cable to better position the implant 100 within the intradiscal space. To remove the cable 200, it is only necessary for the surgeon to apply tension to the opposite end of the cable 200, as shown in FIG. 23. This tension causes the enlarged section 210 to pass through the first cable cavity 202 due to the difference in diameter noted above. The rest of the cable easily passes through all three cavities 202, 204, 206 as necessary, and the cable 200 is thereby easily removed.

With continuing reference to FIGS. 20-23, still referring to FIGS. 20-23 it should be noted that the inventor contemplates various design modifications to the embodiment. For example, other posts than those illustrated could be used to receive the cable 200. It should also be noted that the particular position and orientation of the cavities 202, 204, 206 can vary within sound engineering judgment. Thus, it is not necessary that the cavities 202, 204, 206 be formed through the center of the posts 126, 128. It is also not necessary for the cavities 202, 204, 206 to lie on a plane perpendicular to the axes of the posts 126, 128 as shown. It is also not necessary that the cable 200 and the cavities 202, 204, 206 have circular cross sections as they could be of any shape chosen with sound engineering judgment. It is also contemplated to use any of a number of ways of achieving the enlarged section 210 of the cable 200. For instance, a separate piece such as a washer could be attached to the cable 200 at that point and serve to prevent the cable 200 from being received within the third cable cavity 206.

Figure 13:
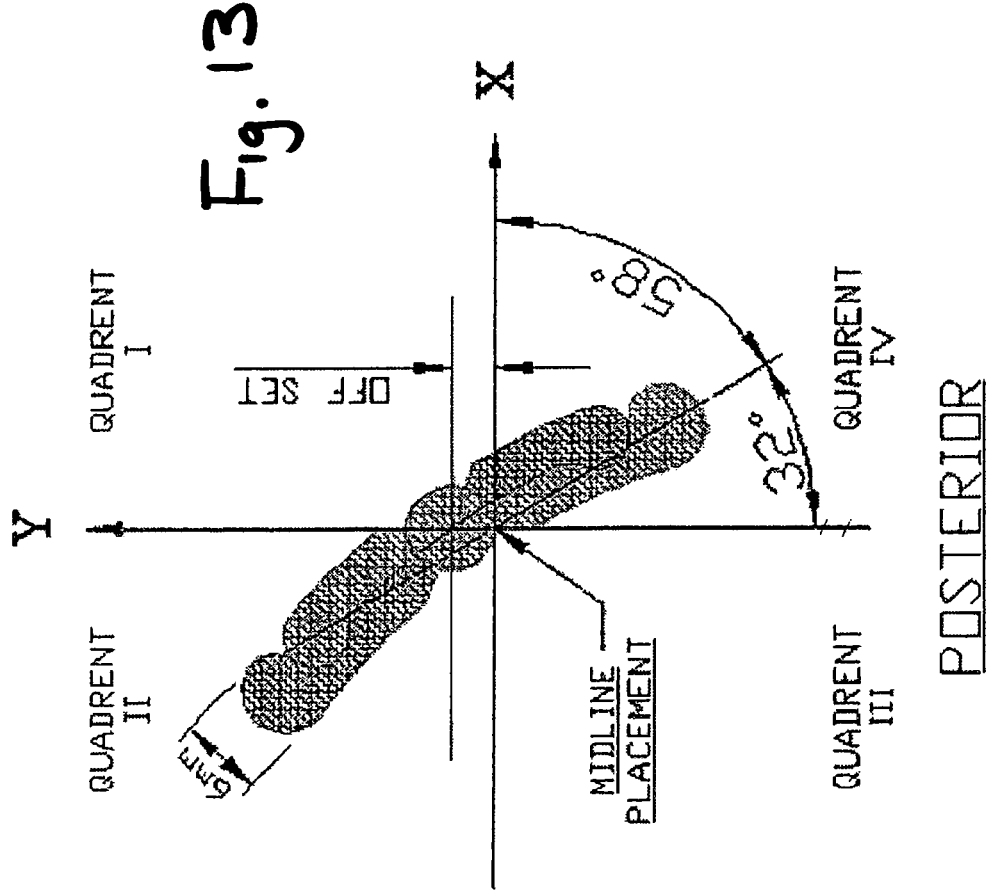
FIG. 13 is a top view of the implant in the non-expanded, non-deployed condition and aligned in a four quadrant system.
Figure 14:
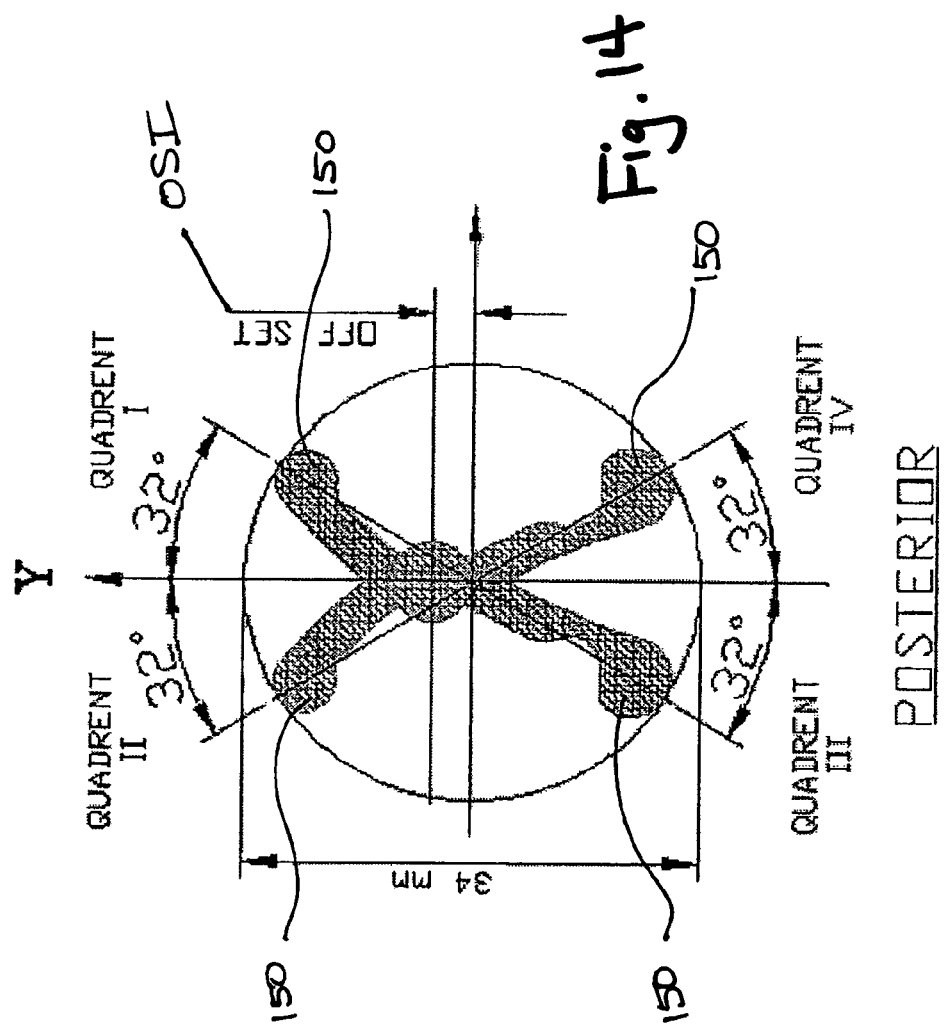
FIG. 14 is a view similar to that shown in FIG. 13, but with the implant shown in the expanded, deployed condition.

With reference now to FIGS. 1, 2, 4, 13 and 14, to assist in understanding how the implant 100 may be inserted, aligned and deployed with respect to the intradiscal space 22, it is helpful to illustrate the implant 100 in a four quadrant system, labeled Quadrants I, II, III and IV. FIG. 13 shows the implant 100 in the first non-expanded condition and FIG. 14 shows the implant 100 in the second expanded condition. When in the expanded condition, the implant 100 lies in all four quadrants, with one pod 150 positioned in each quadrant. The location of the pods 150 within their respective quadrants is dependent on the radii of curvature of the implant 100 and also on the overall length, or sizing of the implant 100. The particular radius of curvature for an implant is variable, selected on the basis of preoperative templating and confirmed and/or amended by intraoperative measurements using needle-tipped sounds and intraoperative biplanar fluoroscopic imaging. To insert the implant 100 using a posterior/posterolateral entry passage, see FIG. 13, the implant 100 is placed into quadrant IV and on into the center of the intradiscal space 22. The implant 100 is advanced past the midpoint of the intradiscal space 22 with an off-set OS1 in the Y-axis direction but centered in the midline, about the Y-axis, as shown. Once placed in this position, the implant 100 can be deployed so that the pods 150 and limbs 144, 146 of the second member 104 migrate away from the pods 150 and limbs 144, 146 of the first member 102 in a scissor-like action. The trailing limb in quadrant IV (for a right sided posterior entry to the disc space) is where the inserter is affixed, holding this limb 144, 146 along the axis of rotation. Full deployment of the implant 100 is achieved when the central axis has locked via the locking mechanism 156 as described above.

With reference now to FIGS. 1-5, the basic surgical technique for placing the implant 100 as an interbody fusion device into an intradiscal space 22 between two adjacent vertebral bodies 12, 14 using minimally invasive surgical (MIS) techniques will now be described. In this technique the intradiscal space 22 may be approached using universally accepted methods for either anterolateral, posterior, or posterolateral (transforaminal) discectomy. Because the implant 100 has such a small, nondeployed (non-expanded) profile, formal facetectomy does not need to be done in order for either an oblique or coronal orientation of the implant 100 within the intradiscal space 22. Assuming a standard approach to the posterior/posterolateral annulus of the targeted disc, appropriate retraction of the neighboring neural structures is accomplished with universally available nerve root retractors. For a posterior/posterolateral approach this would include retraction of the dural sac towards the midline and retraction of the adjacent cephalad and caudad nerve roots, as would normally be done for routine discectomy. Upon isolating the annular surface of the targeted disc, variable needle sounds are placed in the intradiscal space 22 with a range of radii of curvature. The range of these sounds would have been selected on the basis of pre-operative templating of available imaging studies, including plain radiographs, CT or MRI imaging. This preoperative templating provides a narrower range of radii for intraoperative confirmation, decreasing trial and error sounding. The objective of this intraoperative needle sound placement is to locate the center of the intradiscal space 22 and the optimal radii of curvature for the implant 100. The placement of this sound would be confirmed via biplanar intraoperative fluoroscopic imaging. Once the surgeon is satisfied with the centralization and radii of curvature of the needle tipped sound, the radii of curvature of the implant 100 is determined. Routine discectomy is carried out using universally accepted instruments.

With continuing reference to FIGS. 1-5, the intradiscal space 22 is then initially distracted with short, straight interbody spacers, progressively sized until sufficient annular tension is achieved. Once this point is reached, longer, variable radii, curvilinear box chisels may be advanced into the intradiscal space 22 to remove disc material and cartilaginous endplate. Once a majority of intradiscal material is removed, an endplate cutter may be advanced to the entry point to make graduated cuts in the periphery of the endplate to remove the previously referenced normal concave tapering of the bony endplate towards the periphery of the vertebrae. This process would insure true distraction of the intradiscal space 22 from the center. A central distractor is then placed and distraction to the selected level of annular tension is achieved. The degree of this distraction would be based on surgeon preference and/or the intradiscal space 22 height of neighboring non-degenerative discs. With this optimal distraction, further discectomy, or removal of disc material, may be accomplished. The distractor is then placed at the presumed center of the intradiscal space 22 and centralized placement confirmed by intraoperative fluoroscopic imaging. Adjustments, if necessary, may be made in anterior-posterior and medial-lateral orientation until centralization of the distractor is confirmed.

Still referring to FIGS. 1-5, trial spacers of variable heights may then placed with the intradiscal space 22 to select the implant 100 height. Alternatively, the implant height could be selected on the basis of preoperative templating and/or directly from the caliper gauge of the distractor. The implant 100 is then selected corresponding to the radii of curvature of the intraoperative needle tipped sounds, the distractor tips and the trial spacer height. The length of the implant 100 is selected on the basis of surgeon preference and/or operative templating. Once the appropriate sized implant 100 is selected, it is affixed to the inserter handle at one of its ends in the non-expanded, nested, non-deployed state and moved to the intradiscal space 22. Both the central distractor and the inserter may be color-coded and etched with markings corresponding to the selected sizes. The implant 100 may then be impacted into the intradiscal space 22 until the markings are aligned, indicating full seating of the implant 100. Biplanar fluoroscopic imaging may be used to confirm placement of the distractor and fill seating of the implant 100. Adjustments, if necessary, can be made at this time by adjusting the amount of distraction and/or orientation of the distractor in the axial or frontal planes, in a manner described above.

With reference now to FIGS. 1-5, 13-14 and 20-23, once full seating of the implant 100 in the midline is confirmed (with the previously described off-set OS1 if necessary), the implant 100 is deployed into the expanded condition having a second, larger effective footprint area A1/A2. Deployment may be accomplished by applying tension to the cable 200 and thereby pivoting the second member 108 with respect to the first member 106. Alternatively, deployment may be accomplished by impacting a leading edge of the implant 100, along its central axis. Once the second member 108 is pivoted the sufficient distance for the particular implant 100, the locking mechanism 156 automatically engages and the second member 108 is locked in place with respect to the first member 106. At this point, confirmation of satisfactory implant 100 alignment within the intradiscal space 22 may be confirmed by intraoperative biplanar fluoroscopic imaging. Adjustments, if necessary, can be made at this time by changing the degree of distraction and medial-lateral and anterior-posterior translation of the implant 100 by impaction/retraction or rotation with the inserter still in place. Impaction of the distractor against the implant 100 would cause rotation of the implant 100 along its central axis to effect changes in alignment relative to the initial entry angle of the distractor tips, giving the surgeon wide-latitude in final positioning of the implant 100.

With reference now to FIGS. 1-8, once satisfactory implant 100 alignment is achieved, the distractor is released and removed and the inserter disengaged. With the implant 100 now in its fully expanded, deployed state, bone grafting is completed by packing in the open profile of the implant 100. An end cap, formed of silicon or other appropriate material, that affixes to the inserter may then be impacted on the trailing limbs of the implant 100 to prevent migration of bone graft/synthetic bone graft and/or other non-specified osteobiologic materials back into the spinal cord 28 area. This completes the contemplated procedure for implantation of the implant 100. If gross mal-position of the implant 100 were encountered or removal otherwise necessary, the procedure would be reversed and the inserter placed back on the implant 100. Once the inserter is back in place, a removal tool that engages the leading edge of the implant 100 and locks back to the trailing limb at the inserter is used to compress and cause shearing of the pin(s), collapsing the implant 100 back into its non-expanded, non-deployed state. The implant 100 could then be removed with a slap hammer attached to the inserter handle, facilitated if necessary by insertion into the intradiscal space 22 of the central distractor.

Figure 15:
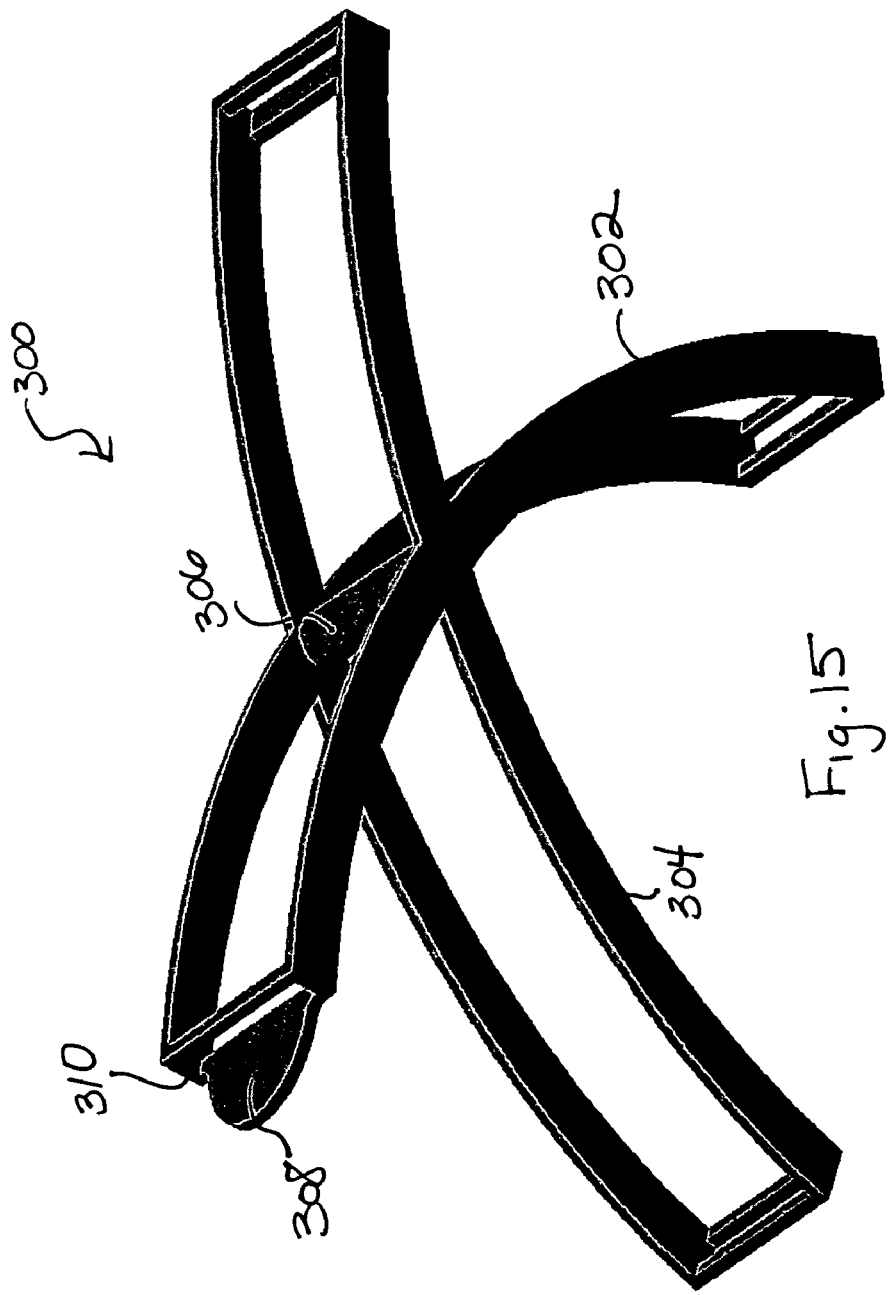
FIG. 15 is a perspective view of an alternate implant embodiment shown in an expanded, deployed condition.
Figure 17:
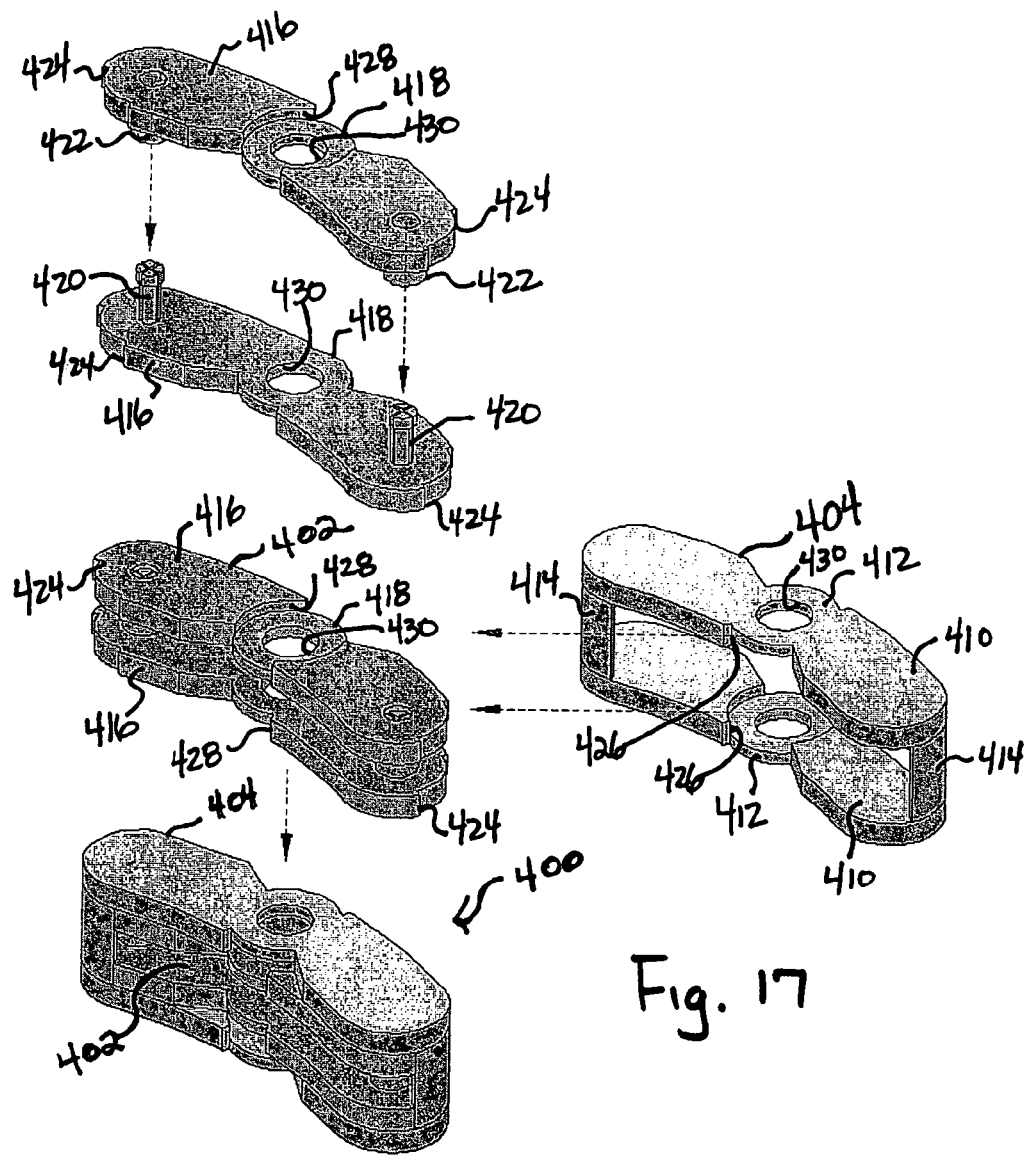
FIG. 17 is an assembly drawing of the implant embodiment shown in FIGS. 16a, 16b and 16c.
Figure 18:
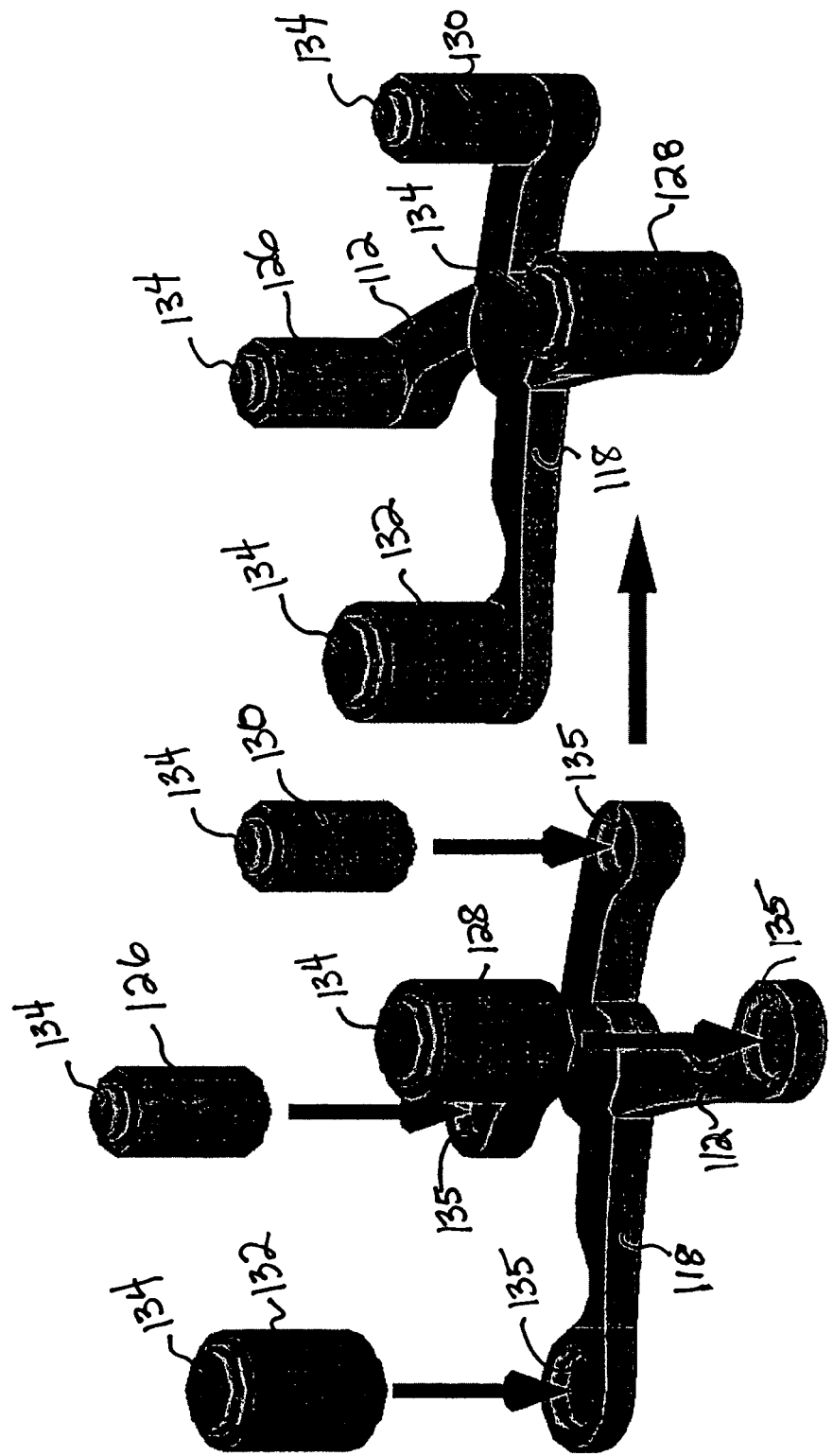
FIG. 18 is an assembly drawing illustrating one embodiment of how the posts may attach to the beams.

With reference now to FIG. 15, an alternate embodiment for an implant 300 is illustrated. The basic operation of this implant 300 is similar the previously described implant 100 in that a first member 302 is pivotal with respect to a second member 304 from a non-expanded condition, to the deployed, expanded condition, shown in FIG. 15. Thus, only the important differences will be discussed. Note first, that for this implant 300 the first member 302 pivots with respect to the second member 304 about a pivot post 306 that may be centrally located, as shown. Note also that the trailing edge of the first member 302 may include a tip or tab 308 and a slot 310. The surgeon may use an inserter or distractor of conventional design to engage the tab 308 and/or slot 310 and thereby deploy the implant 300.

With reference now to FIGS. 16a, 16b, 16c and 17, another alternate embodiment implant 400 illustrated. As with the earlier described embodiments, this embodiment also includes a first member 402 which is pivotal with respect to a second member 404 from a non-deployed or closed condition (shown in FIG. 16a) to a fully deployed, expanded condition (shown in FIG. 16c). For this embodiment the outer surfaces 406 of the first member 402 are spaced inwardly from the outer surfaces 408 of the second member 404 when the implant 400 is in the non-expanded condition. This provides for a very efficient nesting and greatly reduces the width of the implant 400. The second member 404 may include a pair of beams 410, 410 each having a mid-section 412, as shown, connected together with a pair of walls 414, 414. The walls 414, 414 may be positioned at the outer ends of the beams 410 and may be curved to match the shape of the outer ends of the beams 410, as shown.

With continuing reference to FIGS. 16a, 16b, 16c and 17, the first member 402 may include a pair of beams 416, 416 each having a mid-section 418. The beams 416, 416 may be connected together with a pair of posts 420 fixed at one end to one beam 416 and having opposite ends received within openings formed in receiving members 422, 422 extending from the opposite beam 416, as shown. The posts 420 may be spring loaded to urge the beams 416, 416 away from each other. The ends of the beams 416, 416 may have cut out sections 424 to receive the walls 414 when the implant 400 is in the non-expanded condition. This improves the nesting capabilities of the implant 400. The mid-sections 412 of the beams 410 may have notches 426 facing toward the beams 416 and the mid-sections 418 of the beams 416 may have notches 428 facing toward the beams 410, as shown. The purpose for these notches 426, 428 will be described further below. The mid-sections 412, 418 may also have holes 430 formed therethrough. These holes 430 reduce the material necessary to form the beams 410, 416 and also provide additional space to add bone graft material after the implant 400 has been deployed.

Still referring to FIGS. 16a, 16b, 16c and 17, to deploy the implant 400 from the non-deployed condition, shown in FIG. 16a, the first member 402 is pivoted with respect to the second member 404, as shown in FIG. 16b. As noted above, the posts 420 may be spring loaded to urge the beams 416, 416 away from each other. The beams 416, 416, however, cannot yet achieve their fully expanded condition. As the first member 402 continues to be pivoted with respect to the second member 404, the notches 426 in the beams 410 align with the notches 428 in the beams 416. With this alignment the posts 420 extend fully within the receiving members 422 and the beams 416, 416 achieve their fully expanded condition. This also means that the implant 400 is thus placed into the fully deployed condition, as shown in FIG. 16c.

Figure 8:
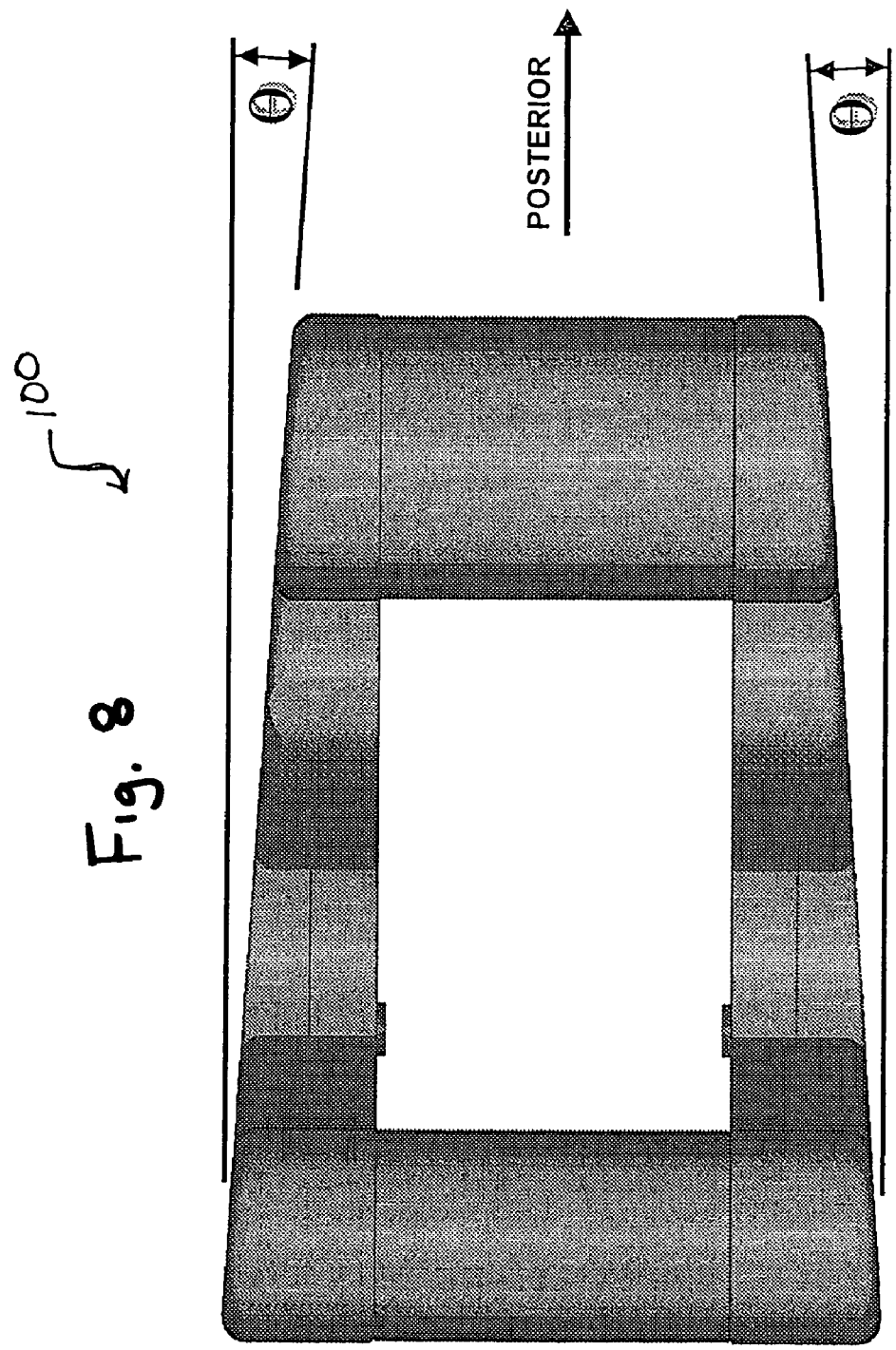
FIG. 8 is a side view of an alternate embodiment showing lordotic taper.

With reference now to FIG. 8, another embodiment is shown. In this case, the embodiment is very similar to and operates in the same manner as the implant 100 described above. In this case, however, the implant 100 is tapered to allow for lordotic taper. In the lordotic taper mode, the height of the implant 100 would be greater in quadrants I and II than in quadrants III and IV, with the height tapering gradually at angle theta from front to back, as shown. This lordotic taper mimics the natural lordotic taper of most intradiscal spaces from anterior to posterior (front to back). Of course other tapering angles and shapes are possible with this invention.

While the embodiments disclosed include the pivoting motion of one member with respect to another member to achieve the expanded condition and thus the increased effective footprint, it is noted that other devices and corresponding methods of expanding the endplate footprint of an implant are also contemplated. Once such device, for example, is an implant that can be inflated to achieve the expanded footprint. It should also be noted that while the implant embodiments provided are all of the "scissor" movement type, other shapes and forms of movement could work equally well with this invention.

With reference to all the FIGURES, all the implant embodiments may be formed of any material that is appropriate for insertion into an intradiscal space, including, but not limited to metal, metal alloy, titanium, titanium alloy, ceramic, carbon-fiber, PEEK or any other osteobiologic or inert, biocompatible material.

In the illustrated embodiments described so far, the focus has been on a minimally invasive, deployable, expandable interbody fusion device. However, it is understood that the present invention has utility in implanting other types of devices including, but not limited to, threaded, non-threaded fusion devices, threaded and non-threaded spacers, and cylindrical, or non-cylindrical devices, disc replacement devices, and osteobiologic material. One embodiment allows for flexible, or motion-preserving articulation between the top and bottom beams to allow for the possibility of load-sharing between the implant and the host bone of the adjacent vertebrae. This enhances bonegraft consolidation and/or healing and maintenance of overall motion at the segment. It should also be noted that according to still another aspect of this invention, the implant can be used as an artificial disc replacement by replacing the solid members of the implant with visco-elastic or motion segments. This allows for use of the device as a motion-preservation device, either constrained or unconstrained. Such a motion-preservation device can be achieved either through the entire length of the beams or solely through the pods.

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

We claim:

1. An implant comprising:
a first member comprising first and second beams;
a first post connecting a first end of the first beam of the first member to a first end of the second beam of the first member;
a second post connecting a second end of the first beam of the first member to a second end of the second beam of the first member;
wherein the first and second posts are the only connections between the first beam of the first member and the second beam of the first member;
a second member comprising first and second beams;
a third post connecting a first end of the first beam of the second member to a first end of the second beam of the second member;
a fourth post connecting a second end of the first beam of the second member to a second end of the second beam of the second member;
wherein the third and fourth posts are the only connections between the first beam the second member and the second beam of the second member;
wherein the first beam of the first member is pivotally connected to the first beam of the second member and the second beam of the first member is pivotally connected to the second beam of the second member;
wherein the first and second members have a first contact surface adapted to contact the endplate of a first vertebral body and a second contact surface adapted to contact the endplate of a second vertebral body adjacent the first vertebral body;
wherein the implant is selectively deployable, when positioned within an intradiscal space between the first and second vertebral bodies, from a first non-expanded condition where the first contact surface has a first effective footprint area A1 to a second expanded condition where the first contact surface has a second effective footprint area A2, the ratio A2/A1 is at least 1.05; and,
wherein the distance between the first and second contact surfaces when the implant is in the first non-expanded condition is substantially equal to the distance between the first and second contact surfaces when the implant is in the second expanded condition.

2. The implant of claim 1 wherein:
an outer surface of the first beam of the first member and an outer surface of the first beam of the second member define the first contact surface; and,
an outer surface of the second beam of the first member and an outer surface of the second beam of the second member define the second contact surface.

3. The implant of claim 1 wherein the first and second contact surfaces are serrated.

4. The implant of claim 1 wherein:
the first beam of the first member has a midsection that is substantially circular in cross-section and the first beam of the second member has a midsection that is substantially circular in cross-section; and,
a pivotal connection is created by juxtaposing the substantially circular midsection of the first beam of the first member with the substantially circular midsection of the first beam of the second member.

5. An implant comprising:
a first member comprising first and second beams;
a first post connecting a first end of the first beam of the first member to a first end of the second beam of the first member;
a second post connecting a second end of the first beam of the first member to a second end of the second beam of the first member;
a second member comprising first and second beams;
a third post connecting a first end of the first beam of the second member to a first end of the second beam of the second member;
a fourth post connecting a second end of the first beam of the second member to a second end of the second beam of the second member;
wherein the first beam of the first member is pivotally connected to the first beam of the second member and the second beam of the first member is pivotally connected to the second beam of the second member;
wherein at least one of the beams has first and second limbs;
wherein flared pods are defined at the end of each limb;
wherein the first and second members have a first contact surface adapted to contact the endplate of a first vertebral body and a second contact surface adapted to contact the endplate of a second vertebral body adjacent the first vertebral body;
wherein the implant is selectively deployable, when positioned within an intradiscal space between the first and second vertebral bodies, from a first non-expanded condition where the first contact surface has a first effective footprint area A1 to a second expanded condition where the first contact surface has a second effective footprint area A2, the ratio A2/A1 is at least 1.05; and,
wherein the distance between the first and second contact surfaces when the implant is in the first non-expanded condition is substantially equal to the distance between the first and second contact surfaces when the implant is in the second expanded condition.

6. The implant of claim 5 wherein each of the beams has first and second limbs.

7. The implant of claim 5 wherein each pod is bulbous with an end that is tapered with a chamfer type profile.

8. An implant comprising:
a first member comprising first and second beams;
a first post connecting a first end of the first beam of the first member to a first end of the second beam of the first member;
a second post connecting a second end of the first beam of the first member to a second end of the second beam of the first member;
a second member comprising first and second beams;
a third post connecting a first end of the first beam of the second member to a first end of the second beam of the second member;
a fourth post connecting a second end of the first beam of the second member to a second end of the second beam of the second member;
wherein the first beam of the first member is pivotally connected to the first beam of the second member and the second beam of the first member is pivotally connected to the second beam of the second member;
wherein at least one of the beams has first and second limbs and the first limb is substantially longer than the second limb;
wherein the first and second members have a first contact surface adapted to contact the endplate of a first vertebral body and a second contact surface adapted to contact the endplate of a second vertebral body adjacent the first vertebral body;
wherein the implant is selectively deployable, when positioned within an intradiscal space between the first and second vertebral bodies, from a first non-expanded condition where the first contact surface has a first effective footprint area A1 to a second expanded condition where the first contact surface has a second effective footprint area A2, the ratio A2/A1 is at least 1.05; and,
wherein the distance between the first and second contact surfaces when the implant is in the first non-expanded condition is substantially equal to the distance between the first and second contact surfaces when the implant is in the second expanded condition.

9. The implant of claim 8 wherein flared pods are defined at the end of each limb and the first limb is longer than the second limb by a distance substantially equal to the width of either pod.

10. An implant comprising:
a first member;
a second member that is selectively pivotal with respect to the first member;
wherein the first and second members have a first contact surface adapted to contact the endplate of a first vertebral body and a second contact surface adapted to contact the endplate of a second vertebral body adjacent the first vertebral body;
wherein the implant is selectively deployable, when positioned within an intradiscal space between the first and second vertebral bodies, from a first non-expanded condition where the first contact surface has a first effective footprint area A1 to a second expanded condition where the first contact surface has a second effective footprint area A2, the ratio A2/A1 is at least 1.05;
wherein the first member is nested with respect to the second member when the implant is in the first non-expanded condition;
wherein the first member comprises first and second beams;
wherein a first post connects a first end of the first beam of the first ember to a first end of the second beam of the first member;
wherein a second post connects a second end of the first beam of the first member to a second end of the second beam of the first member;
wherein the second member comprises first and second beams;
wherein a third post connects a first end of the first beam of the second member to a first end of the second beam of the second member;
wherein a fourth post connects a second end of the first beam of the second member to a second end of the second beam of the second member;
wherein the first beam of the first member is pivotally connected to the first beam of the second member and the second beam of the first member is pivotally connected to the second beam of the second member;
wherein the first beam of the first member has first and second limbs and the first limb is substantially longer than the second limb;
wherein the first beam of the second member has first and second limbs and the first limb is substantially longer than the second limb;
wherein the first limb of the first beam of the first member has a groove;
wherein the first limb of the first beam of the second member has a groove;
wherein the second limb of the first beam of the first member has a pod;
wherein the second limb of the first beam of the second member has a pod;
wherein the pod of the second limb of the first beam of the first member is at least partially received in the groove of the first limb of the first beam of the second member when the implant is in the first non-expanded condition; and,
wherein the pod of the second limb of the first beam of the second member is at least partially received in the groove of the first limb of the first beam of the first member when the implant is in the first non-expanded condition.

* * * * *